US006177491B1

(12) United States Patent
Galbo et al.

(10) Patent No.: US 6,177,491 B1
(45) Date of Patent: Jan. 23, 2001

(54) BLOCK OLIGOMERS CONTAINING 1-HYDROCARBYLOXY-2,2,6,6-TETRAMETHYL-4-PIPERIDYL GROUPS AS STABILIZERS FOR ORGANIC MATERIALS

(75) Inventors: James Peter Galbo, Wingdale, NY (US); Dario Lazzari, Casalecchio di Reno; Fabrizio Guizzardi, Bologna, both of (IT)

(73) Assignee: Ciba Specialty Chemicals Corporation, Tarrytown, NY (US)

( * ) Notice: Under 35 U.S.C. 154(b), the term of this patent shall be extended for 0 days.

(21) Appl. No.: 09/424,140

(22) PCT Filed: May 25, 1998

(86) PCT No.: PCT/EP98/03061

§ 371 Date: Nov. 18, 1999

§ 102(e) Date: Nov. 18, 1999

(87) PCT Pub. No.: WO98/54173

PCT Pub. Date: Dec. 3, 1998

(30) Foreign Application Priority Data

May 27, 1997 (EP) .................................................. 97810327

(51) Int. Cl.$^7$ ........................ C08K 5/3492; C07D 401/12
(52) U.S. Cl. ........................... 524/100; 524/97; 544/113; 544/198; 544/219; 544/220; 252/401; 252/403
(58) Field of Search ..................................... 252/401, 403; 524/97, 100; 544/113, 198, 219, 220

(56) References Cited

U.S. PATENT DOCUMENTS

| 4,086,204 | 4/1978 | Cassandrini et al. | 260/45.8 |
|---|---|---|---|
| 4,234,707 | 11/1980 | Rody et al. | 525/437 |
| 4,331,586 | 5/1982 | Hardy | 525/186 |
| 4,335,242 | 6/1982 | Wiezer et al. | 544/198 |
| 4,459,395 | 7/1984 | Cantatore | 524/100 |
| 4,492,791 | 1/1985 | Orban et al. | 544/198 |
| 5,004,770 | 4/1991 | Cortolano et al. | 524/99 |
| 5,204,473 | 4/1993 | Winter et al. | 546/188 |

FOREIGN PATENT DOCUMENTS

| 19613982 | 10/1996 | (DE) . |
|---|---|---|
| 0053775 | 6/1982 | (EP) . |
| 0209127 | 1/1987 | (EP) . |
| 0357223 | 3/1990 | (EP) . |
| 0377324 | 7/1990 | (EP) . |
| 0462069 | 12/1991 | (EP) . |
| 0782994 | 7/1997 | (EP) . |
| 2301106 | 11/1996 | (GB) . |

Primary Examiner—Kriellion Sanders
(74) Attorney, Agent, or Firm—Tyler A. Stevenson

(57) ABSTRACT

Compounds of formula (I), wherein n is a number from 2 to 14; $R_1$ is for example $C_1$–$C_{18}$alkyl or $C_5$–$C_{12}$cycloalkyl; $R_2$ is for example $C_2$–$C_{12}$alkylene; A is for example acetyl, ($C_1$–$C_4$alkoxy)carbonyl, ($C_1$–$C_4$alkyl)aminocarbonyl or $C_1$–$C_4$alkyl; B is —$OR_3$, —$N(R_4)(R_5)$ or a group of formula (II); $R_3$, $R_4$ and $R_5$, which are identical or different, are for example hydrogen or $C_1$–$C_{18}$alkyl, or —$N(R_4)(R_5)$ is additionally a group of formula (III) with Y being —O—, —$CH_2$—, —$CH_2CH_2$— or >N—$CH_3$; X is —O— or >N—$R_6$; $R_6$ is for example hydrogen or $C_1$–$C_{18}$alkyl; and R is preferably a group of formula (IV); with the proviso that in the individual recurrent units of formula (I), each of the radicals B, R, $R_1$ and $R_2$ has the same or a different meaning. The indicated compounds are useful as light stabilizers, heat stabilizers and oxidation stabilizers for organic materials, in particular synthetic polymers.

27 Claims, 2 Drawing Sheets

BLOCK OLIGOMERS CONTAINING 1-HYDROCARBYLOXY-2,2,6,6-TETRAMETHYL-4-PIPERIDYL GROUPS AS STABILIZERS FOR ORGANIC MATERIALS

The present invention relates to block oligomers containing 1-hydrocarbyloxy-2,2,6,6-tetramethyl-4-piperidyl groups, to their use as light stabilizers, heat stabilizers and oxidation stabilizers for organic materials, particularly synthetic polymers, and to the organic materials thus stabilized.

The stabilization of synthetic polymers with derivatives of 2,2,6,6-tetramethylpiperidine has been described for example in U.S. Pat. Nos. 4,086,204, 4,331,586, 4,335,242, 4,234,707, 4,459,395, 4,492,791, 5,204,473, EP-A 53 775, EP-A-357 223, EP-A-377 324, EP-A-462 069, EP-A-782 994 and GB-A-2 301 106.

The present invention relates in particular to a compound of the formula (I)

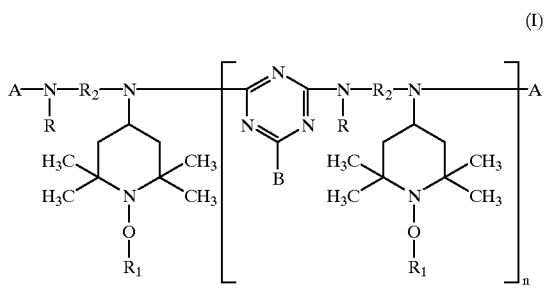

(I)

wherein n is a number from 2 to 14;
the radicals $R_1$ are independently of one another hydrogen or a hydrocarbyl radical or —O—R, is oxyl; the radicals $R_2$ are independently of one another $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_4$ given below except hydrogen; or $R_2$ is a group of the formula (a), (b) or (c);

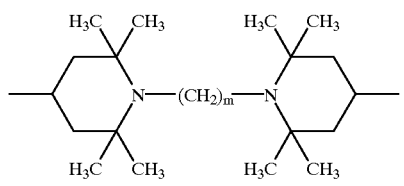

(a)

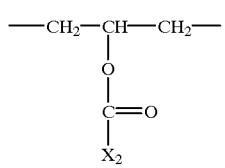

(b)

(c)

with m being 2 or 3,
$X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and
the radicals $X_3$ being independently of one another $C_2$–$C_{12}$alkylene;
the radicals A are independently of one another $C_1$–$C_8$acyl, ($C_1$–$C_8$alkoxy)carbonyl, ($C_5$–$C_{12}$cycloalkoxy)carbonyl, ($C_1$–$C_8$alkyl)aminocarbonyl, ($C_5$–$C_{12}$cycloalkyl)aminocarbonyl, ($C_7$–$C_9$phenylalkyl)aminocarbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; or —$CH_2CN$;
B is —$OR_3$, —$N(R_4)(R_5)$ or a group of the formula (II);

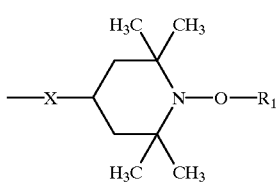

(II)

$R_3$, $R_4$ and $R_5$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

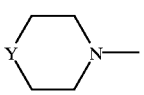

(III)

with Y being —O—, —$CH_2$—, —$CH_2CH_2$— or >N—$CH_3$, or —$N(R_4)(R_5)$ is additionally a group of the formula (III);
X is —O— or >N—$R_6$;
$R_6$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV),

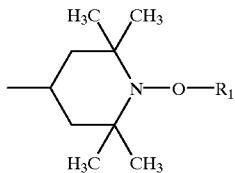

(IV)

or $C_2$–$C_4$alkyl which is substituted in the 2, 3 or 4 position by —OH, $C_1$–$C_8$alkoxy, di($C_1$–$C_4$alkyl)amino or a group of the formula (III); and
the radicals R have independently of one another one of the meanings given for $R_6$;
with the proviso that in the individual recurrent units of the formula (I), each of the radicals B, R, $R_1$ and $R_2$ has the same or a different meaning.

In the individual recurring units of the formula (I), each of the radicals B, R, $R_1$ and $R_2$ has preferably the same meaning.

In the formula (I), the radical R and the radical

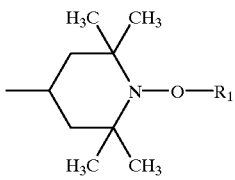

can have a random distribution or a block distribution. $R_1$ as a hydrocarbyl radical of preferably 1 to 18 carbon atoms is e.g. $C_1$–$C_{18}$alkyl, $C_5$–$C_{18}$alkenyl, $C_5$–$C_{18}$alkynyl, $C_5$–$C_{12}$cycloalkyl unsubstituted or substituted by $C_1$–$C_4$alkyl; $C_5$–$C_{12}$cycloalkenyl unsubstituted or substituted by $C_1$–$C_4$alkyl; a bicyclic or tricyclic hydrocarbyl having 6 to 10 carbon atoms or $C_7$–$C_9$phenylalkyl unsubstituted or substituted on the phenyl by $C_1$–$C_4$alkyl.

Examples of alkyl containing not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl. $R_1$ is preferably $C_1$–$C_{12}$alkyl, e.g. $C_6$–$C_{12}$alkyl, in particular heptyl or octyl. $R_6$ is preferably $C_1$–$C_8$alkyl, in particular $C_1$–$C_4$alkyl. One of the preferred meanings of A is $C_1$–$C_4$alkyl.

An example of $C_2$–$C_4$alkyl substituted by —OH is 2-hydroxyethyl.

Examples of $C_2$–$C_4$alkyl substituted by $C_1$–$C_8$alkoxy, preferably by $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$–$C_4$alkyl substituted by di($C_1$–$C_4$alkyl)amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

The group of the formula (III) is preferably

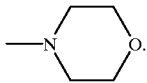

Preferred examples of $C_2$–$C_4$alkyl substituted by a group of the formula (III) are groups of the formula

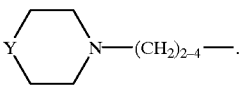

The group

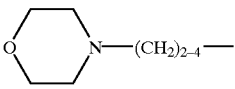

is particularly preferred.

Examples of $C_5$–$C_{12}$cycloalkyl which is unsubstituted or substituted by 1, 2 or 3 $C_1$–$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Unsubstituted or substituted cyclohexyl is preferred.

A preferred example of a bicyclic or tricyclic hydrocarbyl having 6 to 10 carbon atoms is 1,2,3,4-tetrahydronaphthenyl.

A preferred example of $C_5$–$C_{12}$cycloalkenyl unsubstituted or substituted by $C_1$–$C_4$alkyl is cyclohexenyl.

Examples of alkenyl containing not more than 18 carbon atoms are allyl, 2-methylallyl, butenyl, hexenyl, undecenyl and octadecenyl. Alkenyls in which the carbon atom in the 1-position is saturated are preferred.

A preferred example of $C_5$–$C_{18}$alkynyl is octynyl.

Examples of phenyl substituted by 1, 2 or 3 $C_1$–$C_4$alkyl or $C_1$–$C_4$alkoxy are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_9$phenylalkyl which is unsubstituted or substituted on the phenyl by 1, 2 or 3 $C_1$–$C_4$alkyl are benzyl, methylbenzyl, dimethylbenzyl, trimethylbenzyl, t-butylbenzyl and 2-phenylethyl. Benzyl is preferred.

Examples of acyl (aliphatic, cycloaliphatic or aromatic) containing not more than 12 carbon atoms are formyl, acetyl, propionyl, butyryl, pentanoyl, hexanoyl, heptanoyl, octanoyl and benzoyl. $C_1$–$C_8$Alkanoyl and benzoyl are preferred. Acetyl is especially preferred.

Examples of alkoxycarbonyl are methoxycarbonyl, ethoxycarbonyl, propoxycarbonyl, butoxycarbonyl, pentoxycarbonyl, hexoxycarbonyl, heptoxycarbonyl, octoxycarbonyl, nonyloxycarbonyl, decyloxycarbonyl, undecyloxycarbonyl and dodecyloxycarbonyl.

A particularly preferred example of ($C_5$–$C_{12}$cycloalkoxy)carbonyl is cyclohexoxycarbonyl. ($C_5$–$C_7$cycloalkoxy)carbonyl is preferred.

Examples of ($C_1$–$C_8$alkyl)aminocarbonyl are methylaminocarbonyl, ethylaminocarbonyl, propylaminocarbonyl, butylaminocarbonyl, pentylaminocarbonyl, hexylaminocarbonyl, heptylaminocarbonyl and octylaminocarbonyl. ($C_1$–$C_4$alkyl)aminocarbonyl is preferred.

A particularly preferred example of ($C_5$–$C_{12}$cycloalkyl)aminocarbonyl is cyclohexylaminocarbonyl. ($C_5$–$C_7$cycloalkyl)aminocarbonyl is preferred.

A particularly preferred example of ($C_7$–$C_9$phenylalkyl)aminocarbonyl is benzylaminocarbonyl.

Examples of alkylene containing not more than 12 carbon atoms are ethylene, propylene, trimethylene, tetramethylene, pentamethylene, hexamethylene, octamethylene, decamethylene and dodecamethylene. $R_2$ is for example $C_2$–$C_8$alkylene or $C_4$–$C_8$alkylene, in particular $C_2$–$C_6$alkylene, preferably hexamethylene.

An example of $C_4$–$C_{12}$alkenylene is 3-hexenylene.

An example of $C_5$–$C_7$cycloalkylene is cyclohexylene.

Examples of $C_4$–$C_{12}$alkylene interrupted by 1,4-piperazinediyl are

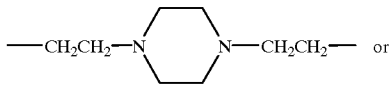

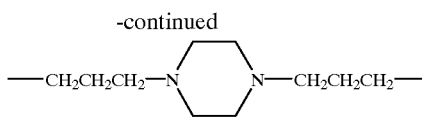

Examples of $C_4$–$C_{12}$alkylene interrupted by —O—, e.g. 1, 2 or 3 —O—, are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl, 3,6,9-trioxaundecane-1,11-diyl and 4,7,10-trioxatridecane-1,13-diyl.

Examples of $C_4$–$C_{12}$alkylene interrupted by >N—$X_1$ are —$CH_2CH_2CH_2$—N($X_1$)—$CH_2CH_2$—N($X_1$)—$CH_2CH_2CH_2$—, in particular —$CH_2CH_2CH_2$—N($CH_3$)—$CH_2CH_2$—N($CH_3$)—$CH_2CH_2CH_2$—.

An example of $C_5$–$C_7$cycloalkylenedi($C_1$–$C_4$alkylene) is cyclohexylenedimethylene.

Examples of $C_1$–$C_4$alkylenedi($C_5$–$C_7$cycloalkylene) are methylenedicyclohexylene and isopropylidenedicyclohexylene.

An example of phenylenedi($C_1$–$C_4$alkylene) is phenylenedimethylene.

The variable n is preferably a number from 2 to 8, in particular 2 to 6.

R is preferably hydrogen, $C_1$–$C_{10}$alkyl, cyclohexyl or a group of the formula (IV), in particular a group of the formula (IV).

$R_1$ is preferably hydrogen, $C_1$–$C_{18}$alkyl, $C_5$–$C_{18}$alkenyl, $C_5$–$C_{18}$alkynyl, $C_5$–$C_{12}$cycloalkyl unsubstituted or substituted by $C_1$–$C_4$alkyl; $C_5$–$C_{12}$cycloalkenyl unsubstituted or substituted by $C_1$–$C_4$alkyl; a bicyclic or tricyclic hydrocarbyl having 6 to 10 carbon atoms or $C_7$–$C_9$phenylalkyl unsubstituted or substituted on the phenyl by $C_1$–$C_4$alkyl; or —O—R, is oxyl.

$R_1$ is in particular hydrogen, $C_1$–$C_8$alkyl, $C_5$–$C_8$cycloalkyl unsubstituted or substituted by methyl; cyclohexenyl, α-methylbenzyl or 1,2,3,4-tetrahydronaphthenyl; for example methyl, octyl or cyclohexyl.

A is preferably acetyl, ($C_1$–$C_4$alkoxy)carbonyl, ($C_1$–$C_4$alkyl)aminocarbonyl or $C_1$–$C_4$alkyl, in particular acetyl or ($C_1$–$C_4$alkyl)aminocarbonyl.

The radical B is preferably a group

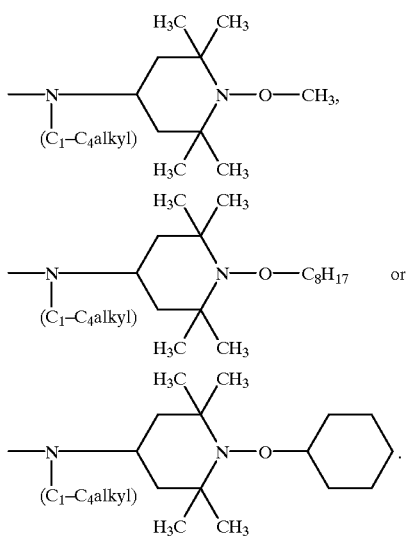

Preferred is a compound of the formula (I), wherein
$R_2$ is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene) or phenylenedi($C_1$–$C_4$alkylene);

A is $C_1$–$C_8$acyl, ($C_1$–$C_8$alkoxy)carbonyl, ($C_5$–$C_7$cycloalkoxy)carbonyl, ($C_1$–$C_4$alkyl)aminocarbonyl, ($C_5$–$C_7$cycloalkyl)aminocarbonyl, benzylaminocarbonyl, $C_1$–$C_6$alkyl, $C_5$–$C_7$cycloalkyl, allyl or benzyl;

$R_3$, $R_4$ and $R_5$, which are identical or different, are hydrogen, $C_1$–$C_{12}$alkyl, $C_5$–$C_7$cycloalkyl which is unsubstituted or substituted by 1, 2 or 3 $C_1$–$C_4$alkyl; $C_3$–$C_{12}$alkenyl, phenyl which is unsubstituted or substituted by 1, 2 or 3 $C_1$–$C_4$alkyl; benzyl which is unsubstituted or substituted on the phenyl by $C_1$–$C_4$alkyl; tetrahydrofurfuryl or $C_2$–$C_3$alkyl which is substituted in the 2 or 3 position by —OH, $C_1$–$C_4$alkoxy, di($C_1$–$C_4$alkyl)amino or a group of the formula (III); or —N($R_4$)($R_5$) is additionally a group of the formula (III); and $R_6$ is hydrogen, $C_1$–$C_{12}$alkyl, $C_5$–$C_7$cycloalkyl which is unsubstituted or substituted by 1, 2 or 3 $C_1$–$C_4$alkyl; benzyl which is unsubstituted or substituted on the phenyl by 1, 2 or 3 $C_1$–$C_4$alkyl; tetrahydrofurfuryl, a group of the formula (IV) or $C_2$–$C_3$alkyl which is substituted in the 2 or 3 position by —OH, $C_1$–$C_4$alkoxy, di($C_1$–$C_4$alkyl)amino or a group of the formula (III).

Also preferred is a compound of the formula (I), wherein $R_2$ is $C_2$–$C_8$alkylene;

A is $C_1$–$C_8$acyl, ($C_1$–$C_8$alkoxy)carbonyl, cyclohexoxycarbonyl, ($C_1$–$C_4$alkyl)aminocarbonyl, cyclohexylaminocarbonyl, benzylaminocarbonyl, $C_1$–$C_4$alkyl, cyclohexyl, allyl or benzyl;

$R_3$, $R_4$ and $R_5$, which are identical or different, are hydrogen, $C_1$–$C_8$alkyl, cyclohexyl which is unsubstituted or substituted by methyl; $C_3$–$C_8$alkenyl, phenyl which is unsubstituted or substituted by methyl; benzyl, tetrahydrofurfuryl or $C_2$–$C_3$alkyl substituted in the 2 or 3 position by —OH, $C_1$–$C_4$alkoxy, dimethylamino, diethylamino or 4-morpholinyl; or —N($R_4$)($R_5$) is additionally 4-morpholinyl; and $R_6$ is hydrogen, $C_1$–$C_8$alkyl, cyclohexyl which is unsubstituted or substituted by methyl; benzyl, tetrahydrofurfuryl, a group of the formula (IV) or $C_2$–$C_3$alkyl substituted in the 2 or 3 position by —OH, $C_1$–$C_4$alkoxy, dimethylamino, diethylamino or 4-morpholinyl.

A further preferred compound of the formula (I) is that wherein n is a number from 2 to 6;
R is a group of the formula (IV);
$R_2$ is $C_2$–$C_6$alkylene;
A is $C_1$–$C_8$acyl, ($C_1$–$C_8$alkoxy)carbonyl, ($C_1$–$C_4$alkyl)aminocarbonyl, $C_1$–$C_4$alkyl or allyl;
B is —N($R_4$)($R_5$) or a group of the formula (II);
$R_4$ and $R_5$, which are identical or different, are hydrogen, $C_1$–$C_8$alkyl, 2-hydroxyethyl or 2-methoxyethyl or —N($R_4$)($R_5$) is additionally 4-morpholinyl;
X is >$NR_6$; and
$R_6$ is $C_1$–$C_4$alkyl.

A particularly preferred compound of the formula (I) is that wherein n is a number from 2 to 6;
R is a group of the formula (IV);
$R_1$ is methyl, octyl or cyclohexyl;
$R_2$ is $C_2$–$C_6$alkylene;
A is $C_1$–$C_8$acyl, ($C_1$–$C_8$alkoxy)carbonyl, ($C_1$–$C_4$alkyl)aminocarbonyl or $C_1$–$C_4$alkyl;
B is —N($R_4$)($R_5$) or a group of the formula (II);
$R_4$ and $R_5$, which are identical or different, are $C_1$–$C_8$alkyl or —N($R_4$)($R_5$) is additionally 4-morpholinyl;

X is >NR$_6$; and
R$_6$ is C$_1$–C$_4$alkyl.

Also particularly preferred is a compound of the formula (I), wherein
n is a number from 2 to 6;
R is a group of the formula (IV);
R$_1$ is methyl, octyl or cyclohexyl;
R$_2$ is C$_2$–C$_6$alkylene;
A is C$_1$–C$_8$acyl or (C$_1$–C$_4$alkyl)aminocarbonyl;
B is a group of the formula (II);
X is >NR$_6$; and
R$_6$ is C$_1$–C$_4$alkyl.

Polydispersity indicates the molecular-weight distribution of a polymeric compound. In the present application, the polydispersity is the ratio of weight-average ($\overline{M}w$) and number-average ($\overline{M}n$) molecular weights. A value of $\overline{M}w/\overline{M}n$ equal to 1 means that the compound is monodispers and has only one molecular weight and no molecular weight distribution. A narrow molecular weight distribution is characterized by a polydispersity $\overline{M}w/\overline{M}n$ close to 1.

In general, the compounds of this invention are not limited by the polydispersity $\overline{M}w/\overline{M}n$ The compound corresponding to the formula (I) may be a monodispers compound having a polydispersity $\overline{M}w/\overline{M}n$ of 1 with n being 2, 3, 4, 5, 6, 7, 8, 9, 10, 11, 12, 13 or 14 or a polydispers compound with a molecular weight distribution. Such a polydispers compound corresponds for example to a mixture containing at least three different monodispers compounds of the formula (I), which vary only by the variable n. The polydispersity $\overline{M}w/\overline{M}n$ of the mixture is for example 1.1 to 1.7, 1.1 to 1.65, 1.1 to 1.6, 1.1 to 1.55 or 1.1 to 1.5. n is preferably 2, 4 and 6 in this mixture.

Further examples for the polydispersity $\overline{M}w/\overline{M}n$ are 1.2 to 1.7, for example 1.2 to 1.65, 1.2 to 1.6, 1.2 to 1.55 or 1.2 to 1.5.

The compounds of this invention may be prepared, for example, according to the following methods.

METHOD 1): Using starting materials already containing groups of the formula (IV).

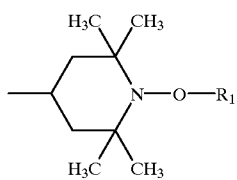

(IV)

METHOD 2): Using a block oligomer of the formula (I-0) as starting material wherein n, A and R$_2$ have the meanings given above and R* and B* are defined herein later;

and transferring the groups of the formula (IV-0)

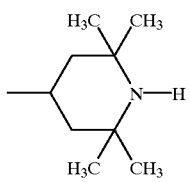

(IV-0)

being present in the block oligomer to groups of the formula (IV).

The mixture described above may be prepared according to METHOD 1) by 1) reacting a compound of the formula (α)

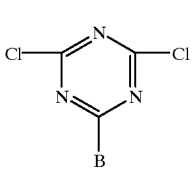

(α)

with a compound of the formula (β)

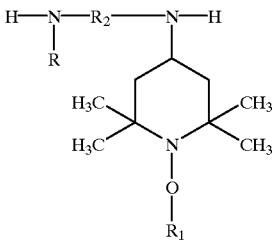

(β)

in a stoichiometric ratio to obtain a compound of the formula (γ);

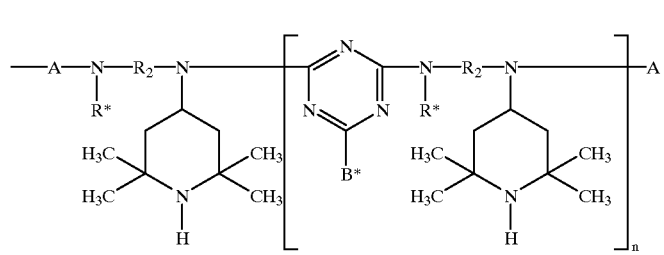

(I-0)

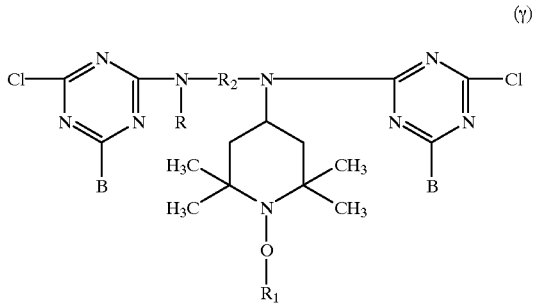

(γ)

2) reacting a compound of the formula (γ) with a compound of the formula (β) in a molar ratio of 1:2 to 1:3, preferably 1:2 to 1:2.5, in particular in a molar ratio of 1:2, to obtain a mixture of at least three different monodispers compounds of the formula (δ) with n being 2, 3, 4, 5, 6, 7, 8, 9, 10, 11, 12, 13 or 14 or being 2, 3, 4, 5, 6, 7, 8, 9, 10, 11 or 12, preferably 2, 3, 4, 5, 6, 7, 8, 9 or 10, or preferably 2, 3, 4, 5, 6, 7 or 8, in particular 2, 4 and 6;

When A is a methyl group, the compounds of the formula (I) can also be obtained by reacting a mixture of formaldehyde/formic acid with a compound of the formula (δ) as described for example in U.S. Pat. No. 5 130 429 or in U.S. Pat. No. 3,898,303.

Examples for suitable organic solvents are toluene, xylene, trimethylbenzene, isopropylbenzene, diisopropylbenzene and essentially water-insoluble organic ketones such as, for example, methyl isobutyl ketone. Xylene is preferred.

Examples for an inorganic base are sodium hydroxide, potassium hydroxide, sodium carbonate and potassium carbonate. Sodium hydroxide is preferred. When the radical B in the formula (α) is a group of the formula (II) with X being oxygen, it is appropriate to use sodium carbonate or potassium carbonate as inorganic base in the reactions 1) and 2).

The reaction 1) is carried out, for example, at a temperature of 40° C. to 70° C., preferably 50° C. to 60° C.

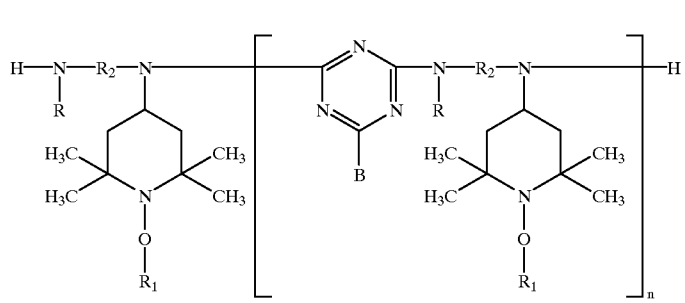

(δ)

3) reacting the mixture obtained in 2) with a compound of the formula (ε) or with a compound of the formula (ζ)

A'—X'  (ε)

A"—NCO  (ζ)

in about a stoichiometric ratio to obtain the desired mixture; the radicals R, $R_1$, $R_2$ and B are as defined above;
X' is a leaving group, for example halogen, in particular chlorine;
A' is $C_1$–$C_8$acyl, ($C_1$–$C_8$alkoxy)carbonyl, ($C_5$–$C_{12}$cycloalkoxy)carbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl;
or —$CH_2CN$; and
A" is $C_1$–$C_8$alkyl, $C_5$–$C_{12}$cycloalkyl or $C_7$–$C_9$phenylalkyl;
the reactions 1) to 3) are carried out in an organic solvent in the presence of an inorganic base with the proviso that, when in the reaction 3) a compound of the formula (ζ) is applied, said reaction 3) is carried out without any inorganic base.

When A is $C_1$–$C_8$acyl, the reaction 3) may also be carried out with the corresponding acid anhydride as reagent instead of a compound of the formula (ε).

The reaction 2) is carried out, for example, at a temperature of 110° C. to 180° C., preferably 140° C. to 160° C.

When the reactant of the formula (ε) is used in the reaction 3), said reaction 3) is carried out, for example, at a temperature of 60° C. to 180° C., preferably 146° C. to 160° C., if necessary in a closed vessel.

When the reactant of the formula (4) is used in the reaction 3), said reaction 3) is carried out, for example, at a temperature of 0° C. to 60° C., preferably 0° C. to 25° C.

Possible by-products are the compounds of the formulae (Id) and (Ie).

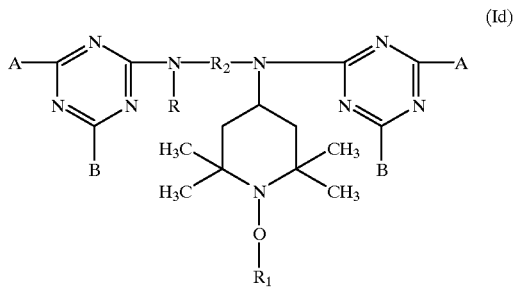

(Id)

-continued

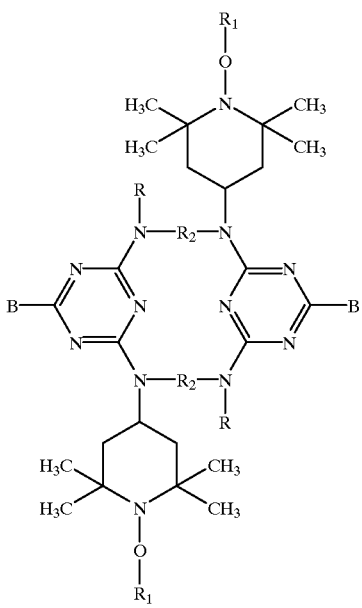

(Ie)

Each of these compounds may be present in the mixture in an amount of, for example, up to 30 mol %, preferably up to 20 mol %, up to 10 mol % or up to 8 mol %, relative to the total mixture.

The compound of the formula (α) can be prepared, for example, by reacting cyanuric chloride with a compound B—H in a stoichiometric ratio in the presence of an organic solvent and an inorganic base.

It is appropriate to use for the preparation of the compounds of the formula (α) the same solvent and the same inorganic base as in the above indicated reactions 1) to 3).

In general, the starting materials used in the above process are known. In the case that they are not commercially available, they can be prepared analogously to known methods.

For the preparation of the starting material of the formula (α) with B being a group of the formula (II) as well as for the preparation of the starting material of the formula (β) it is appropriate to use, for example, compounds of the formula (S-I).

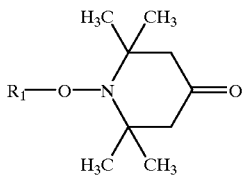

(S-I)

The compounds of the formula (S-I) may be prepared, for example, by reacting 1-oxyl-2,2,6,6-tetramethyl-4-piperidone with a hydroperoxide, preferably t-butyl hydroperoxide, in the presence of a peroxide decomposing catalyst such as $MoO_3$ in a hydrocarbon solvent. The meaning of $R_1$ depends on the hydrocarbon solvent used. For example, when $R_1$ is cyclohexyl, the hydrocarbon solvent used is cyclohexane. In general, the preparation of the compounds of the formula (S-I) may be carried out analogously to the process described in U.S. Pat. No. 4,921,962 which is incorporated herein by reference.

It is also possible to prepare the compounds of the formula (S-I) by coupling 1-oxyl-2,2,6,6-tetramethyl-4-piperidone with hydrocarbon radicals. The principle of such a reaction is, for example, described by R. L. Kinney et al. in J. Am. Chem. Soc., 1978, 100, 7902–7915 (Reaction of alkyl iodides with tri-n-butyltin hydride) and by D. W. Grattan at al. in Polym. Degrad. and Stability 1979, 69 (Photolysis of a solution of di-tert-butyl peroxide and cyclohexane). The indicated reactions are, for example, disclosed in U.S. Pat. No. 5,021,577 (Examples 5 and 16) as well as in U.S. Pat. No. 5,204,473 (Examples 7 to 10) and can be applied to prepare the compounds of the formula (S-I) by using the appropriate starting materials.

When $R_1$ is methyl, the preparation of the compound of the formula (S-I) is conveniently carried out by reacting 1-oxyl-2,2,6,6-tetramethyl-4-piperidone with hydrogen peroxide in the presence of ferrous sulfate heptahydrate in dimethylsulfoxide, as disclosed for example in U.S. Pat. No. 5,374,729.

The preparation of 1-oxyl-2,2,6,6-tetramethyl-4-piperidone is, for example, described in Nature 196, 472–474, Chemical Abstracts 58: 56264 and Beilstein EIII/IV 21 3279.

The following Examples S-A and S-B illustrate the preparation of the compounds of the formula (S-I) more specifically.

EXAMPLE S-A (starting material):

Preparation of 1-methoxy-2,2,6,6-tetramethyl-4-piperidone.

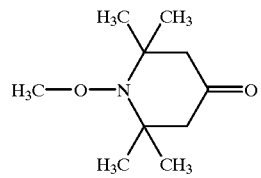

A 5.0 L 4 neck mechanically stirred flask is charged with 1oxyl-2,2,6,6-tetramethyl-4-piperidone (300 g, 1.76 moles), ferrous sulfate heptahydrate (513.7 g, 1.85 moles) and dimethylsulfoxide (1450 g). Hydrogen peroxide, 30% (279.2 g, 2.46 moles), is added over a 1 hour 45 min span. The temperature is maintained at 29–32° C. The content is stirred for an additional 30 min at 25–30° C. and then chilled below 1° C. Water (1250 ml) is added and the mixture is extracted with four 750 ml portions of ethyl acetate. The combined extracts are washed, 2×1.0 L of $H_2O$, then 1×500 ml of saturated NaCl and then dried over anhydrous $MgSO_4$. Ethyl acetate is evaporated and the product is distilled (82–84° C. $10.33×10^{-2}$ bar), yielding 254 g of a pale yellow oil (yield: 78% of theory; IR-spectrum: Ketone carbonyl, 1710 cm-1).

EXAMPLE S-B (starting material):

Preparation of 1-cyclohexyloxy-2,2,6,6-tetramethyl-4-piperidone.

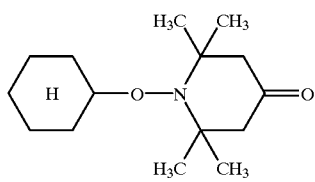

A mixture of cyclohexane (215 ml, 2.0 moles), t-butyl hydroperoxide, 70% aqueous (77.1 g, 0.6 moles), molybdenum trioxide (1.44 g, 0.01 moles) and 1-oxyl-2,2,6,6-tetramethyl-4-piperidone (34 g, 0.2 moles) is charged into a 500 ml flask equipped with a Barrett trap. The mixture is stirred at reflux (80° C.) for two hours until no more water is collected. Then, the mixture is filtered by gravity into a pressure bottle and molybdenum trioxide (1.44 g, 0.01 mole) is added. Subsequently, the mixture is heated under stirring to 105° C. (2.34 bar) and held for 5 hours, until the color changes from deep orange to pale yellow. The mixture is filtered and the clear solution is washed with 10% aqueous sodium sulfite (100 ml) and subsequently with water (2×50 ml). The obtained clear solution is dried over sodium sulfate and then concentrated to give 50 g of the desired material as a clear yellow oil (Mass spectrum: m/e=253)

In more detail, the starting material of the formula (a) with B being a group of the formula (II) corresponds to the formula (α-1)

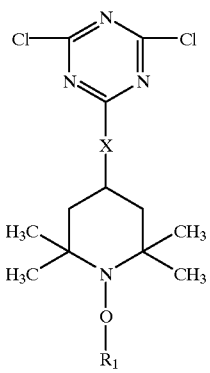

When X is a group >N—R$_6$, such compounds may be prepared, for example, according to Scheme 1 as shown below.

Scheme 1

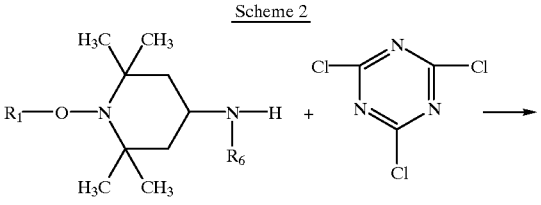

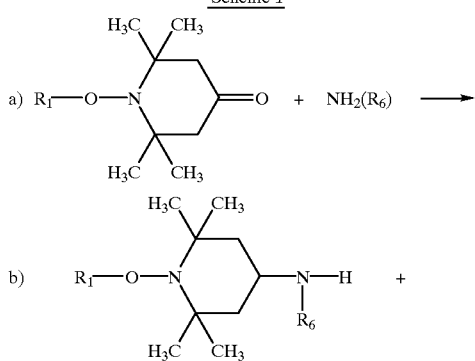

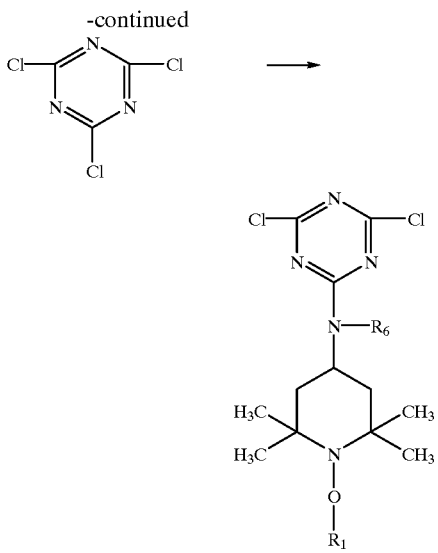

Reaction a) of Scheme 1 may be carried out, for example, analogously to the method described in EP-A-309 402 (in particular Examples 45 and 46) and reaction b) of Scheme 1 may be carried out analogously to the method described in U.S. Pat. No. 4,086,204.

Compounds of the formula (α-I) with X being oxygen may be prepared, for example, according to Scheme 2 as shown below.

Scheme 2

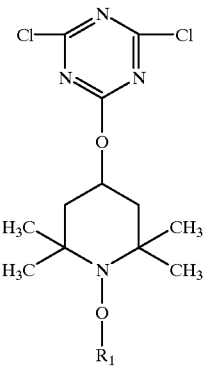

L is for example an alkaline metal salt such as lithium, sodium or potassium. The reaction may be carried out in an inert organic solvent such as toluene, xylene or trimethylbenzene at a temperature of −20° C. to 70° C., preferably 0° C. to 60° C., using the appropriate molar ratio of the reactants.

The compounds of the formula (S-II) may be obtained, for example, by treating the appropriate 4-hydroxypiperidine derivative with an alkaline alcoholate or an alkaline metal in an inert organic solvent such as toluene, xylene or trimethylbenzene at reflux temperature, simultaneously distilling off the alcohol formed during the reaction. The preparation of the 4-hydroxypiperidine derivative can be carried out analogously to the method described in EP-A-309 402 (in particular Example 12).

The starting material of the formula (β) with R being e.g. a group of the formula (IV) may be prepared, for example, according to Scheme 3:

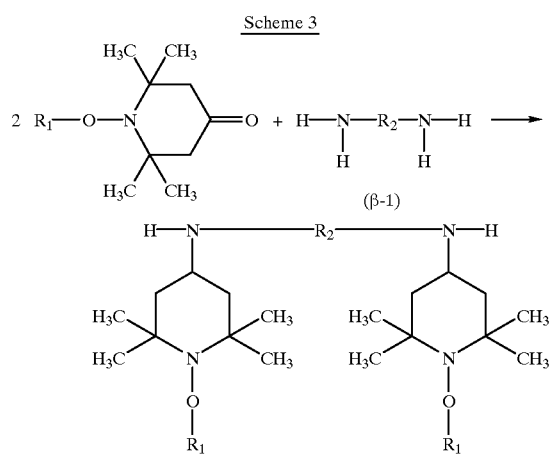

Scheme 3

The reaction can be carried out analogously to the method described in e.g. EP-A-309 402 (in particular Example 45). The compounds of the formula (β-1) are known and most of them are commercially available. Some compounds of the formula (β-1) are described in WO-A-95/21157, U.S. Pat. No. 4,316,837 and U.S. Pat. No. 4,743,688.

A compound of the formula (I) with a polydispersity $\overline{M}w/\overline{M}n$ of 1 may be prepared by building up said compound step by step. A representative example for such a procedure is as follows:

The intermediate of the formula (δ) with n being 2 corresponds to the formula and can be prepared by reacting a compound of the formula (γ) with a compound of the formula (β) in a molar ratio of 1:10 to 1:50, preferably 1:20 to 1:40, in particular 1:20 to 1:35. The reaction may be carried out e.g. in an organic solvent or neat in the presence of an inorganic base. The solvent and/or the excess of the reactant of the formula (β) can be eliminated by distillation at the appropriate conditions. Examples for an organic solvent are toluene, xylene, trimethylbenzene, isopropylbenzene and diisopropylbenzene. Xylene is preferred. Examples for an inorganic base are sodium hydroxide, potassium hydroxide, sodium carbonate and potassium carbonate. Sodium hydroxide is preferred. The reaction is carried out at a temperature of, for example, 110° C. to 180° C., preferably 140° C. to 160° C.

Subsequently, the intermediate obtained is conveniently reacted with an acylating or alkylating agent according to the conditions of the above described reaction 3).

Compounds of the formula (I) which are not characterized by a particular polydispersity can be prepared, for example, by reacting a compound of the formula (α) with an excess of up to 10% by mole of a compound of the formula (β) without controlling the building up of the molecule. Subsequently, the product obtained may be reacted with a compound of the formula (ε) or (ζ) as described above.

A preferred embodiment of this invention relates to a product obtainable by METHOD 2) that means by transferring groups of the formula (IV-0)

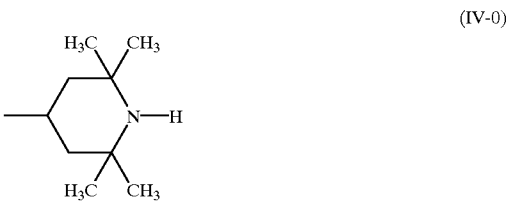

(IV-0)

being present in a block oligomer corresponding to the formula (I-0)

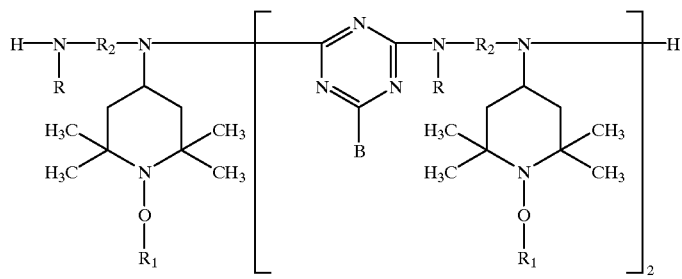

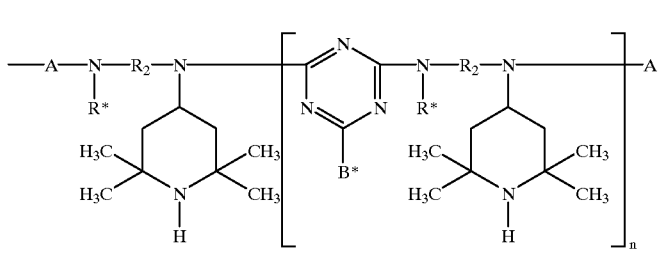

(I-0)

to groups of the formula (IV);

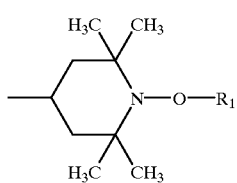

(IV)

wherein $R_1$ is a hydrocarbyl radical or —O—$R_1$ is oxyl; said transfer is carried out by reaction of the block oligomer corresponding to the formula (I-0) with a hydroperoxide in a hydrocarbon solvent in the presence of a peroxide decomposing catalyst;

n is a number from 2 to 14;

the radicals $R_2$ are independently of one another $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi-($C_6$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_4$ given below; or $R_2$ is a group of the formula (a), (b) or (c);

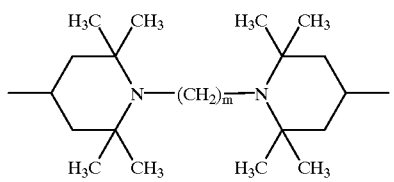

(a)

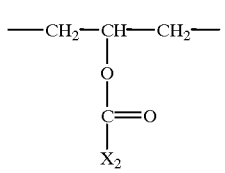

(b)

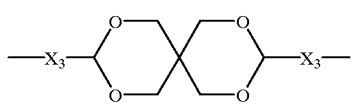

(c)

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

the radicals A are independently of one another $C_1$–$C_8$acyl, ($C_1$–$C_8$alkoxy)carbonyl, ($C_5$–$C_{12}$cycloalkoxy)carbonyl, ($C_1$–$C_8$alkyl)aminocarbonyl, ($C_5$–$C_{12}$cycloalkyl)aminocarbonyl, ($C_7$–$C_9$phenylalkyl)aminocarbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; or —$CH_2CN$;

$B^*$ is —$OR_3$, —$N(R_4)(R_5)$ or a group of the formula (II-0);

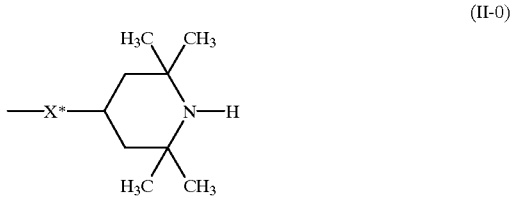

(II-0)

$R_3$, $R_4$ and $R_5$, which are identical or different, are $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

(III)

with Y being —O—, —$CH_2$—, —$CH_2CH_2$— or >N—$CH_3$; and $R_3$ is additionally hydrogen or —$N(R_4)(R_5)$ is additionally a group of the formula (III);

$X^*$ is —O— or >N—$R_6^*$;

$R_6^*$ is $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV-0), or $C_2$–$C_4$alkyl which is substituted in the 2, 3 or 4 position by —OH, $C_1$–$C_8$alkoxy, di($C_1$–$C_4$alkyl)amino or a group of the formula (III); and the radicals $R^*$ have independently of one another one of the meanings given for $R_6^*$;

with the proviso that in the individual recurrent units of the formula (I-0), each of the radicals $B^*$, $R^*$ and $R_2$ has the same or a different meaning.

A preferred embodiment of this invention relates to a product obtainable by METHOD 2), wherein $R_2$ is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by —O— or >N—$X_1$ with $X_1$ being $C_1$–$C_{12}$acyl or ($C_1$–$C_{12}$alkoxy)carbonyl or having one of the definitions of $R_4$; or $R_2$ is a group of the formula (b);

$R_3$, $R_4$ and RE, which are identical or different, are $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and $R_3$ is additionally hydrogen or —N($R_4$)($R_5$) is additionally a group of the formula (III);

$R_6$* is $C_1$–$C_{18}$alkyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; or a group of the formula (IV-0).

Another preferred embodiment of this invention relates to a product obtainable by METHOD 2), wherein $R_2$ is $C_2$–$C_{10}$alkylene, cyclohexylene, cyclohexylenedi($C_1$–$C_4$alkylene), $C_1$–$C_4$alkylene-dicyclohexylene or phenylenedi($C_1$–$C_4$alkylene);

$R_3$, $R_4$ and $R_5$, which are identical or different, are $C_1$–$C_{12}$alkyl, $C_5$–$C_7$cycloalkyl which is unsubstituted or substituted by 1, 2 or 3 $C_1$–$C_4$alkyl; phenyl which is unsubstituted or substituted by 1, 2 or 3 $C_1$–$C_4$alkyl; benzyl which is unsubstituted or substituted on the phenyl by $C_1$–$C_4$alkyl; or —N($R_4$)($R_5$) is additionally a group of the formula (III); and $R_6$* is $C_1$–$C_{12}$alkyl, $C_5$–$C_7$cycloalkyl which is unsubstituted or substituted by 1, 2 or 3 $C_1$–$C_4$alkyl; benzyl which is unsubstituted or substituted on the phenyl by 1, 2 or 3 $C_1$–$C_4$alkyl; or a group of the formula (IV-0).

Also a preferred embodiment of this invention is a product obtainable by METHOD 2), wherein $R_2$ is $C_2$–$C_6$alkylene;

B* is —N($R_4$)($R_5$) or a group of the formula (II-0);

$R_4$ and $R_5$, which are identical or different, are $C_1$–$C_8$alkyl; or —N($R_4$)($R_5$) is additionally 4-morpholinyl;

X* is >N$R_6$*;

$R_6$* is $C_1$–$C_8$alkyl.

R* is preferably a group of the formula (IV-0) and B* is preferably a group of the formula (II-0) with X* being a group of the formula >N-($C_1$–$C_4$alkyl).

The transfer of the groups of the formula (IV-0) to groups of the formula (IV) may be carried out, for example, analogously to the method described in U.S. Pat. No. 4 921 962 which is incorporated by reference herein.

The meaning of $R_1$ depends on the hydrocarbon solvent used. $R_1$ is preferably a hydrocarbyl radical having 5 to 18 carbon atoms.

$R_1$ is in particular $C_5$–$C_{18}$alkyl, $C_5$–$C_{12}$alkenyl, $C_5$–$C_{18}$alkynyl, $C_5$–$C_{12}$cycloalkyl unsubstituted or substituted by $C_1$–$C_4$alkyl; $C_5$–$C_{12}$cycloalkenyl unsubstituted or substituted by $C_1$–$C_4$alkyl; a bicyclic or tricyclic hydrocarbyl having 6 to 10 carbon atoms or $C_7$–$C_9$phenylalkyl unsubstituted or substituted on the phenyl by $C_1$–$C_4$alkyl; and the hydrocarbon solvent is, dependent on R., $C_5$–$C_{18}$alkane, $C_5$–$C_{18}$alkene, $C_5$–$C_{18}$alkyne, $C_5$–$C_{12}$cycloalkane unsubstituted or substituted by $C_1$–$C_4$alkyl; $C_5$–$C_{12}$cycloalkene unsubstituted or substituted by $C_7$–$C_4$alkyl; a bicyclic or tricyclic hydrocarbon having 6 to 10 carbon atoms or $C_7$–$C_9$phenylalkane unsubstituted or substituted on the phenyl by $C_1$–$C_4$alkyl.

$R_1$ is also preferably heptyl, octyl, cyclohexyl, methylcyclohexyl, cyclooctyl, cyclohexenyl, α-methylbenzyl or 1,2,3,4-tetrahydronaphthenyl, and the hydrocarbon solvent is accordingly, dependent on $R_1$, heptane, octane, cyclohexane, methylcyclohexane, cyclooctane, cyclohexene, ethylbenzene or tetralin.

According to a further preferred embodiment of this invention $R_1$ is cyclohexyl or octyl, and the hydrocarbon solvent is, dependent on $R_1$, cyclohexane or octane.

When —O—$R_1$ is oxyl, the hydrocarbon solvent is conveniently an inert organic solvent, preferably toluene or 1,2-dichloroethane.

The peroxide decomposing catalyst is, for example, a metal carbonyl, metal oxide, metal acetylacetonate or a metal alkoxide where the metal is selected from the groups IVb, Vb, VIb, VIIb and VIII of the periodic table, preferably vanadium (III) acetylacetonate, cobalt carbonyl, chromium (VI) oxide, titanium (IV) isopropoxide, titanium tetrabutoxide, molybdenum hexacarbonyl, molybdenum trioxide and the like. The most preferred catalyst is $MoO_3$.

Suitable hydroperoxides are t-butyl hydroperoxide, t-amyl hydroperoxide, t-hexyl hydroperoxide, t-octyl hydroperoxide, ethylbenzene hydroperoxide, tetralin hydroperoxide or cumene (=isopropylbenzene) hydroperoxide. The most preferred hydroperoxide is t-butyl hydroperoxide.

2 to 8 moles, preferably 3 to 6 moles, of the hydroperoxide, 0.001 to 0.1 mole, preferably 0.005 to 0.05 moles, of the peroxide decomposing catalyst and 5 to 30 moles, preferably 10 to 20 moles, of the hydrocarbon solvent are applied, for example, per mole of the hindered amine moiety of the formula (IV-0)

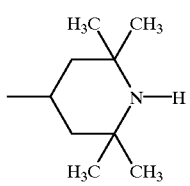

(IV-0)

being present in the block oligomer corresponding to the formula (I-0).

The transfer of the hindered amine moieties of the formula (IV-0) to groups of the formula

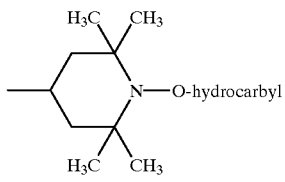

is, for example, carried out at 75° C. to 160° C., preferably 100° C. to 150° C.

When the hindered amine moieties of the formula (IV-0) are first treated with aqueous -hydroperoxide in the presence of the peroxide decomposing catalyst in an inert organic solvent (for example analogously to the method described in U.S. Pat. No. 4,691,015), the initial reaction product obtained in a relatively short time is the corresponding N-oxyl intermediate (—O$R_1$=oxyl) which is highly colored and which can be isolated per se.

When the organic solvent is a hydrocarbon having a labile hydrogen atom, when there remains a sufficient molar excess of hydroperoxide beyond that needed to convert the amine to the corresponding N-oxyl derivative, and when the reaction mixture is heated at moderate temperatures (preferably 100° C. to 150° C.) for an additional period, a further reaction takes place between the N-oxyl compound (either prepared in situ from the original amine or employed as the initial starting intermediate in the process) and the hydrocarbon solvent to give the corresponding N-hydrocarbyloxy derivative.

The original reaction mixture is colorless, but becomes highly colored as the N-oxyl intermediate is formed. This color disappears as the N-oxyl compound is converted into the colorless N-hydrocarbyloxy product. This process thus in essence has a built-in color indicator to show the extent of reaction. When the reaction mixture becomes colorless, it shows that the colored N-oxyl intermediate has been completely converted into the N-hydrocarbyloxy product.

An embodiment of this invention is also a product obtainable by hydrogenating the product obtainable by METHOD 2), wherein —OR$_1$ in the formula (IV) is oxyl, to get a product with groups of the formula (IV-1).

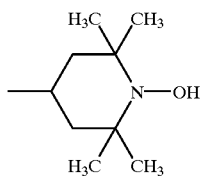

(IV-1)

The hydrogenation is carried out according to known methods, for example in an organic solvent, e.g. methanol or ethanol, in the presence of a hydrogenation catalyst, preferably palladium on carbon or PtO$_2$, as described e.g. in U.S. Pat. No. 4 691,015.

The block oligomer starting material corresponding to the formula (I-0), which is described in U.S. patent application Ser. No. 08/994,977 and EP Patent Application No. 97810989.0 may be a monodispers compound having a polydispersity $\overline{M}w/\overline{M}n$ of 1 with n being an integer such as 2, 3, 4, 5, 6, 7, 8, 9, 10, 11,12, 13 or 14 or a polydispers compound with a molecular weight distribution. Preferably, the block oligomer starting material is a polydispers compound that means for example a mixture containing at least three different monodispers compounds of the formula (I-0), which differ only by the variable n, said mixture having e.g. a polydispersity $\overline{M}w/\overline{M}n$ of a value higher than 1 to a value of 1.7, for example 1.1 to 1.65, 1.1 to 1.6, 1.1 to 1.55 or 1.1 to 1.5; or 1.2 to 1.7, for example 1.2 to 1.65, 1.2 to 1.6, 1.2 to 1.55 or 1.2 to 1.5.

A polydispers block oligomer starting material corresponding to the formula (I-0) having e.g. a polydispersity $\overline{M}w/\overline{M}n$ of a value higher than 1 to a value of 1.7 may be prepared, for example, as follows:

1*) reacting a compound of the formula (α*)

(α*)

with a compound of the formula (β*)

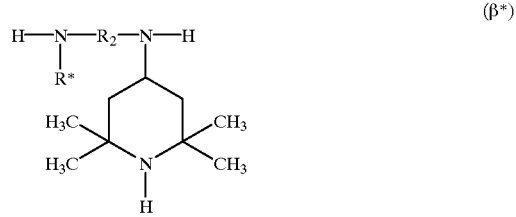

(β*)

in a stoichiometric ratio to obtain a compound of the formula (γ*);

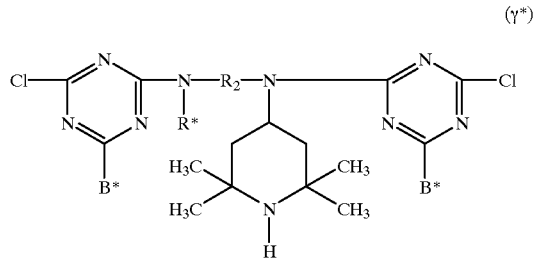

(γ*)

2*) reacting a compound of the formula (γ*) with a compound of the formula (β*) in a molar ratio of 1:2 to 1:3, preferably 1:2, to obtain a mixture of at least three different monodispers compounds of the formula (δ*) with n being 2, 3, 4, 5, 6, 7, 8, 9, 10, 11,12, 13 or 14, in particular 2, 4 and 6;

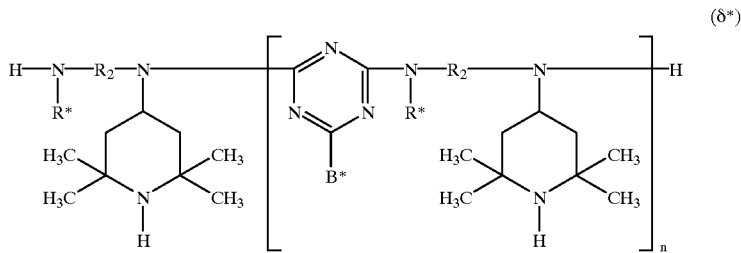

(δ*)

3*) reacting the mixture obtained in 2*) with a compound of the formula (ε) or with a compound of the formula (ζ)

A'—X'     (ε)

A"—NCO    (ζ)

in about a stoichiometric ratio to obtain the desired mixture;
R*, R₂ and B* are as defined in the formula (I-0);
X' is a leaving group, for example halogen, in particular chlorine;
A' is $C_1$–$C_8$acyl, ($C_1$–$C_8$alkoxy)carbonyl, ($C_5$–$C_{12}$cycloalkoxy)carbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl;
or —$CH_2CN$; and
A" is $C_1$–$C_8$alkyl, $C_5$–$C_{12}$cycloalkyl or $C_7$–$C_9$phenylalkyl;
the reactions 1*) to 3*) are carried out in an organic solvent in the presence of an inorganic base with the proviso that, when in the reaction 3*) a compound of the formula (ζ) is applied, said reaction 3*) is carried out without any inorganic base.

The remarks given above under METHOD 1) for the reactions 1) to 3) are also applicable to the reactions 1*) to 3*).

A particularly preferred block oligomer starting material corresponding to the formula (I-0) is a polydispers compound with $\overline{M}w/\overline{M}n$ of e.g. 1.1 to 1.7. Such a polydispers compound is for example a mixture containing at least three monodispers compounds, which differ only in the number of the repetitive units and which are
a) a compound of the formula (SM-Ia),

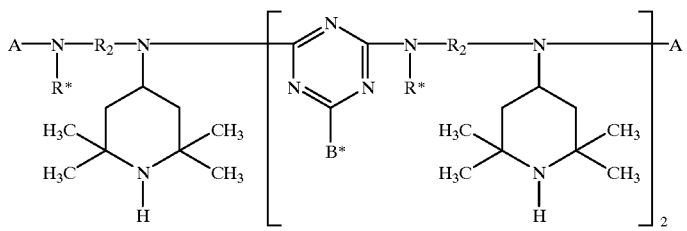

(SM-Ia)

b) a compound of the formula (SM-Ib) and

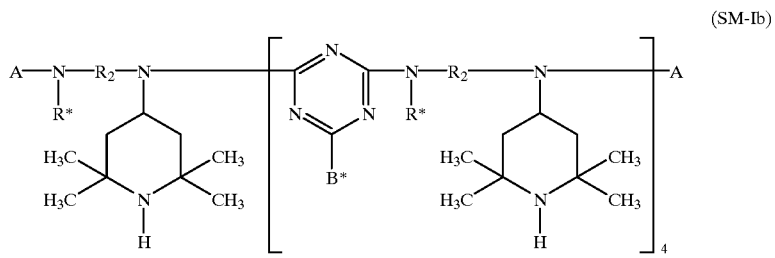
(SM-Ib)

c) a compound of the formula (SM-Ic)

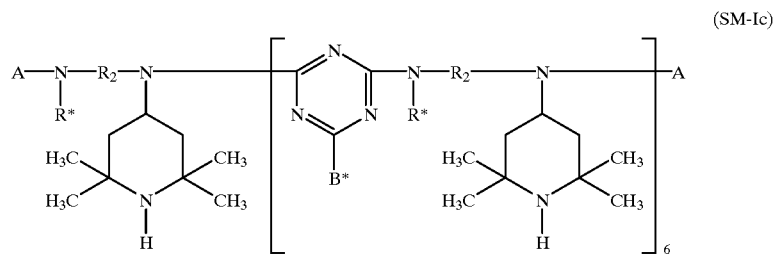
(SM-Ic)

wherein A, B*, R* and $R_2$ are as defined above, and the molar ratio of the compounds of the formula (SM-Ia) to (SM-Ib) to (SM-Ic) is 2:2:1.5 to 2:0.5:0.05, preferably 2:1.5:1 to 2:0.5:0.08, in particular 2:1:0.5 to 2:0.5:0.08.

When using the above shown mixture, containing a compound of the formula (SM-Ia), a compound of the formula (SM-Ib) and a compound of the formula (SM-Ic), as starting material in accordance with METHOD 2), a mixture containing a) a compound of the formula (Ia),

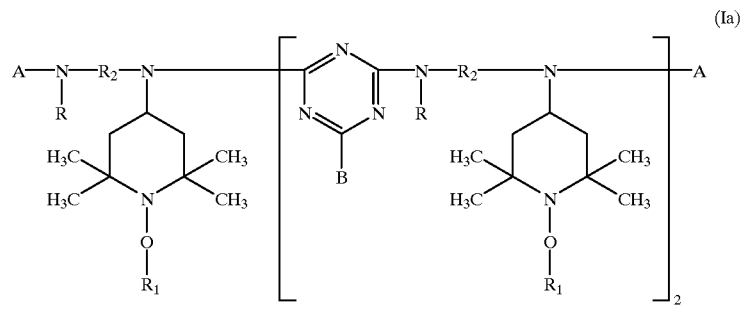
(Ia)

b) a compound of the formula (Ib) and

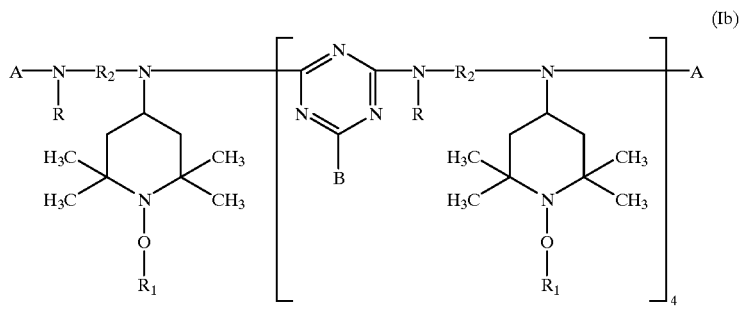

(Ib)

c) a compound of the formula (Ic)

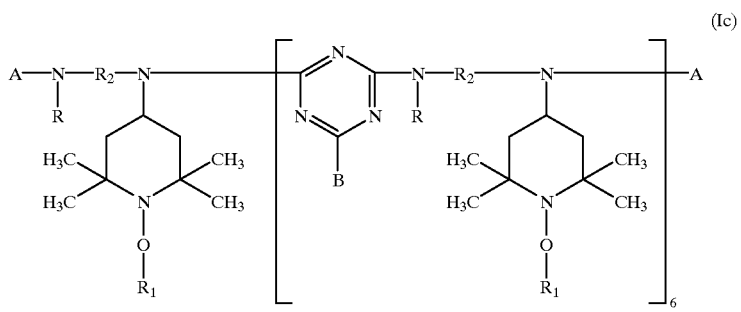

(Ic)

is obtained which is a further embodiment of this invention. The compounds of the formulae (Ia), (Ib) and (Ic) differ only in the number of the repetitive units, the molar ratio of the compounds of the formula (Ia) to (Ib) to (Ic) is 2:2:1.5 to 2:0.5:0.05, preferably 2:1.5:1 to 2:0.5:0.08, in particular 2:1:0.5 to 2:0.5:0.08; and $R_1$ is hydrogen or a hydrocarbyl radical or —O—R, is oxyl;
$R_2$ is $C_2$-$C_{12}$alkylene, $C_4$-$C_{12}$alkenylene, $C_5$-$C_7$cycloalkylene, $C_5$-$C_7$cycloalkylenedi-($C_1$-$C_4$alkylene), $C_1$-$C_4$alkylenedi($C_5$-$C_7$cycloalkylene), phenylenedi($C_1$-$C_4$alkylene) or $C_4$-$C_{12}$alkylene interrupted by 1,4-piperazinediyl, —O— or >N—$X_1$ with $X_1$ being $C_1$-$C_{12}$acyl or ($C_1$-$C_{12}$alkoxy)carbonyl or having one of the definitions of $R_4$ given below, or $R_2$ is a group of the formula (a), (b) or (c);

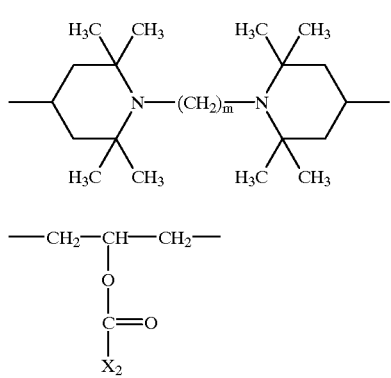

(a)

(b)

-continued

(c)

with m being 2 or 3, $X_2$ being $C_1$-$C_{18}$alkyl, $C_5$-$C_{12}$cycloalkyl which is unsubstituted or substituted by 1, 2 or 3 $C_1$-$C_4$alkyl; phenyl which is unsubstituted or substituted by 1, 2 or 3 $C_1$-$C_4$alkyl or $C_1$-$C_4$alkoxy; $C_7$-$C_9$phenylalkyl which is unsubstituted or substituted on the phenyl by 1, 2 or 3 $C_1$-$C_4$alkyl; and the radicals $X_3$ being independently of one another $C_2$-$C_{12}$alkylene;

A is $C_1$-$C_8$acyl, ($C_1$-$C_8$alkoxy)carbonyl, ($C_5$-$C_{12}$cycloalkoxy)carbonyl, ($C_1$-$C_8$alkyl)aminocarbonyl, ($C_5$-$C_{12}$cycloalkyl)aminocarbonyl, ($C_7$-$C_9$phenylalkyl)aminocarbonyl, $C_1$-$C_8$alkyl, $C_5$-$C_{12}$cycloalkyl which is unsubstituted or substituted by 1, 2 or 3 $C_1$-$C_4$alkyl; $C_3$-$C_6$alkenyl, $C_7$-$C_9$phenylalkyl which is unsubstituted or substituted on the phenyl by 1, 2 or 3 $C_1$-$C_4$alkyl;

or —$CH_2CN$;

B is —OR$_3$, —N(R$_4$)(R$_5$) or a group of the formula (II);

(II)

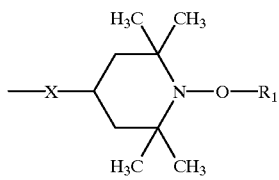

R$_3$, R$_4$ and R$_5$, which are identical or different, are C$_1$–C$_{18}$alkyl, C$_5$–C$_{12}$cycloalkyl which is unsubstituted or substituted by 1, 2 or 3 C$_1$–C$_4$alkyl; C$_3$–C$_{18}$alkenyl, phenyl which is unsubstituted or substituted by 1, 2 or 3 C$_1$–C$_4$alkyl or C$_1$–C$_4$alkoxy; C$_7$–C$_9$phenylalkyl which is unsubstituted or substituted on the phenyl by 1, 2 or 3 C$_1$–C$_4$alkyl; tetrahydrofurfuryl or C$_2$–C$_4$alkyl which is substituted in the 2, 3 or 4 position by —OH, C$_1$–C$_8$alkoxy, di(C$_1$–C$_4$alkyl)amino or a group of the formula (III);

(III)

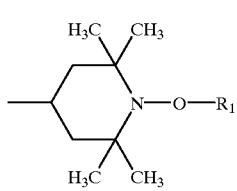

with Y being —O—, —CH$_2$—, —CH$_2$CH$_2$— or >N—CH$_3$; and R$_3$ is additionally hydrogen or —N(R$_4$)(R$_5$) is additionally a group of the formula (III);
X is —O— or >N—R$_6$;
R$_6$ is C$_1$–C$_{18}$alkyl, C$_3$–C$_{18}$alkenyl, C$_5$–C$_{12}$cycloalkyl which is unsubstituted or substituted by 1, 2 or 3 C$_1$–C$_4$alkyl; C$_7$–C$_9$phenylalkyl which is unsubstituted or substituted on the phenyl by 1, 2 or 3 C$_1$–C$_4$alkyl; tetrahydrofurfuryl, a group of the formula (IV), (IV)

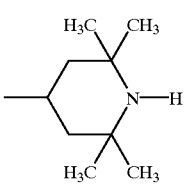

or C$_2$–C$_4$alkyl which is substituted in the 2, 3 or 4 position by —OH, C$_1$–C$_8$alkoxy, di(C$_1$–C$_4$alkyl)amino or a group of the formula (III); and
R has one of the meanings given for R$_6$.
Preferred is a mixture wherein
R is a group of the formula (IV);

(IV)

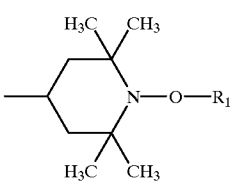

R$_1$ is octyl or cyclohexyl;
R$_2$ is C$_2$–C$_6$alkylene;
A is C$_1$–C$_8$acyl or (C$_1$–C$_4$alkyl)aminocarbonyl;

B is a group of the formula (II);

(II)

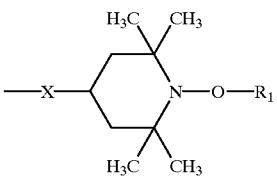

X is >NR$_6$; and
R$_6$ is C$_1$–C$_4$alkyl.
After the transfer of the groups of the formula (IV-0)

(IV-0)

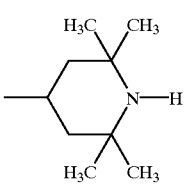

being present in a block oligomer starting material (mixture containing the compounds of the formulae (SM-Ia), (SM-Ib) and (SM-Ic)) to groups of the formula (IV), (IV)

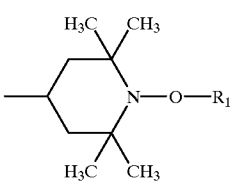

the ratio of the compounds of the formula (Ia) to (Ib) to (Ic) corresponds to the ratio of the above shown initial compounds of the formula (SM-Ia) to (SM-Ib) to (SM-Ic), since the backbone of these compounds is not affected during the reaction.

In the mixtures according to this invention, the radical R. can act as a linking group between two or more block oligomers of the formulae (Ia), (Ib) and/or (Ic). In this case, bridges of the formula (L-I) are formed (L-1)

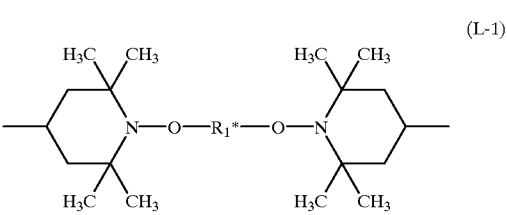

between the indicated block oligomers.

The meaning of R$_1$* can be deduced from the meaning of R$_1$. The only difference between these two radicals is that R$_1$* has one or two additional valences. Thus, R$_1$ as cyclohexyl corresponds to R$_1$* as cyclohexanediyl or cyclohexanethyl and R$_1$ as octyl corresponds to R$_1$* as octanediyl or octanetriyl.

The products of this invention as well as the described mixtures are very effective in improving the light, heat and oxidation resistance of organic materials, especially synthetic polymers and copolymers. In particular, a low pigment interaction as well as a very good colour is observed in polypropylene, especially polypropylene fibres, in particular in the presence of flame retardants as well as in low density polyethylene (LDPE) films for agricultural use. It is further remarkable that the product of this invention is a flame retardant itself.

Examples of organic materials which can be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VII of the Periodic Table. These metals usually have one or more than one ligand, typically oxides, halides, alcoholates, esters, ethers, amines, alkyls, alkenyls and/or aryls that may be either $\pi$- or $\sigma$-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/ styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloridelvinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrilel butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POMlacrylate, POMIMBS, PPO/HIPS, PPO/PA 6.6 and copolymers, PA/HDPE, PNPP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The invention thus also relates to a composition comprising an organic material susceptible to degradation induced by light, heat or oxidation and a product or a mixture according to this invention.

The organic material is preferably a synthetic polymer, more particularly one selected from the aforementioned groups. Polyolefins are preferred and polyethylene and polypropylene are particularly preferred.

A further embodiment of this invention is a method for stabilizing an organic material against degradation induced by light, heat or oxidation, which comprises incorporating into said organic material a product or a mixture according to this invention.

The product or the mixture according to this invention can be used in various proportions depending on the nature of the material to be stabilized, on the end use and on the presence of other additives.

In general, it is appropriate to use, for example, 0.01 to 5% by weight of the product or the mixture according to this invention, relative to the weight of the material to be stabilized, preferably 0.05 to 2%, in particular 0.05 to 1%.

The product or the mixture according to this invention can be added, for example, to the polymeric materials before, during or after the polymerization or crosslinking of the said materials. Furthermore, it can be incorporated in the polymeric materials in the pure form or encapsulated in waxes, oils or polymers.

In general, the product or the mixture according to this invention can be incorporated in the polymeric materials by various processes, such as dry mixing in the form of powder, or wet mixing in the form of solutions or suspensions or also in the form of a masterbatch which contains the product or the mixture according to this invention in a concentration of 2.5 to 25% by weight; in such operations, the polymer can be used in the form of powder, granules, solutions, suspensions or in the form of latices.

The materials stabilized with the product or the mixture according to this invention can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, corrosion inhibitors and metal deactivators, can be added to the organic materials containing the product or the mixture according to this invention.

Particular examples of said conventional additives are:
1. Antioxidants
1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(x-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-di-methyl-6-(1'-methylheptadec-1'-yl)phenol, 2,4-dimethyl-6-(1'-methyltridec-1'-yl)phenol and mixtures thereof.
1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.
1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.
1.4. Tocopherols, for example α-tocopherol, β-tocopherol, γ-tocopherol, δ-tocopherol and mixtures thereof (Vitamin E).
1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.
1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyl-phenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2,6-dihydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.
1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxy-benzyl)sulfide, isooctyl-3,5-di-tert-butyl-4-hydroxybenzylmercaptoacetate.
1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl- 2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.
1.9. Aromatic hydroxybenzyl compounds, for example 1,3,5-tris-(3,5-di-tert-butyl-4-hydroxy-benzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.
1.10 Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxy-benzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.
1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.
1.12. Acylaminophenols, for example 4-hydroxylauranilide, 4-hydroxystearanilide, octyl N-(3,5-di-tert-butyl-4-hydroxyphenyl)carbamate.
1.13. Esters of β-(3.5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.
1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.
1.15. Esters of β-(3.5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.
1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxy-phenylpropionyl)trimethylenediamide, N,N'-bis(3,5-di-tert-butyl-4-hydroxyphenylpropionyl)-hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butylylaminophenol, 4-nonanoylaminophenol, 4-dodecanoylamino-phenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$]$_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyt-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-o-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxy-ethyl)- 2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl) sebacate, bis(1-octyloxy-2,2,6,6-tetrame-thylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5- triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro [4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1.3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxywphenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis (2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-di-benz[d,g]-1,3,2-dioxaphosphocin, 6-fluoro-2,4,8,10-tetra-tert-butyl-1 2-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of O-thiodipropionic acid, for example the lauryl, stearyl, myristyl or tridecyl esters, mercaptobenzimidazole or the zinc salt of 2-mercaptobenzimidazole zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flowcontrol agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl] benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The weight ratio of the product or the mixture according to this invention to the conventional additives may be, for example, 1:0.5 to 1:5.

The products of this invention can also be used as stabilizers, especially as light stabilizers, for almost all materials known in the art of photographic reproduction and other reproduction techniques as e.g. described in Research Disclosure 1990, 31429 (pages 474 to 480).

The invention is illustrated in more detail by the following Examples. All percentages are by weight, unless otherwise indicated.

The following Examples S-1 and S-2 are representative for the preparation of the starting materials. Examples 1 to 4 are representative for the preparation of the products according to this invention and relate to a particular preferred embodiment.

GPC (Gel Permeation Chromatography) is used as an analytical procedure for separating molecules by their difference in size and to obtain molecular weight averages($\overline{Mw}$, $\overline{Mn}$) or information on the molecular weight distribution of polymers.

The technique is well known and described, for instance, in "Modern Size—Exclusion Liquid Chromatography" by W. W. Yan et al., edited by J. Wiley & Sons, N.Y., USA, 1979, pages 4–8, 249–283 and 315–340.

A narrow molecular weight distribution is characterized by a polydispersity ($\overline{Mw}/\overline{Mn}$) close to 1.

The GPC analyses shown in the following Examples S-1 and S-2 are carried out with a GPC chromatograph ®Perkin-Elmer LC 250 equipped with ®Perkin-Elmer RI detector LC 30 and with ®Perkin-Elmer oven LC 101.

All the analyses are carried out at 45° C. by using three columns PLGEL 3 µm Mixed E 300 mm lenghtx7.5 mm i.d.(from Polymers Laboratories Ltd. Shropshire, U.K).

Tetrahydrofurane is used as eluant (flow 0.40 ml/min) and the samples are dissolved in tetrahydrofurane (2%) (% w/v).

In the structural formulae of the following examples, n' indicates that there are repetitive units in the molecules and the products obtained are not uniform.

EXAMPLE S-1

Preparation of a product corresponding to the formula

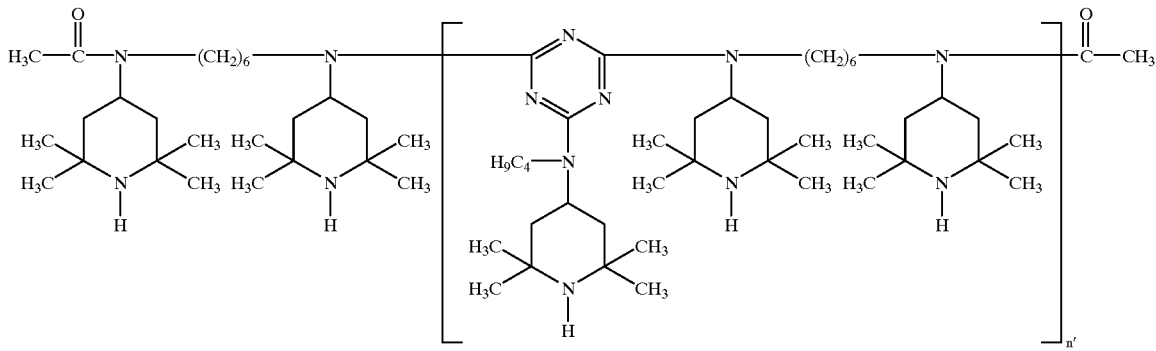

A solution of 37.1 (0.175 moles) of N-(2,2,6,-tetramethyl-4-piperidinyl)-n-butylamine in 30 ml of water is slowly added at 0° C. to a solution of 32.2 g (0.175 moles) of cyanuric chloride in 250 ml of xylene, keeping the temperature during the addition and for further 1 hour.

After 2 hours at room temperature, the mixture is cooled to 0° C. and an aqueous solution of 7.3 g (0.18 moles) of sodium hydroxide in 25 ml of water is added.

After ½ hours at room temperature, the aqueous solution is separated off and 34.6 g (0.087 moles) of N,N'-bis[2,2,6,6-tetramethyl-4-piperidinyl]-1,6-hexanediamine are added.

The mixture is heated to 50° C. for 1 hour a nd 24.2 g (0.175 moles) of ground potassium carbonate are added and heated to 60° C. for 4 hours.

After washing with water, the organic phase is concentrated under vacuum at 60°–70° C./10 mbar, being 125 ml of xylene recovered.

69 g (0.175 moles) of N,N'-bis[2,2,6,6-tetramethyl-4-piperidinyl]-1,6-hexanediamine are added and the mixture is heated to 150° C. for 2 hours, cooled again and 7 g (0.175 moles) of ground sodium hydroxide are added.

The mixture is heated to 140° C. for further 4 hours, being the residual water of reaction eliminated off azeotropically, and for further 4 hours at 160° C.

After cooling to 60° C., the mixture is diluted with 130 ml of xylene, filtered and washed three times with 50 ml of ethylene glycol.

After concentrating under vacuum at 60° C./10 mbar, 7.5 g (0.073 moles) of acetic anhydride are added. After ½ hour at room temperature, the mixture is heated to 130° C. for 5 hours. After cooling to room temperature, 20.2 g (0.146 moles) of ground potassium carbonate are added and the mixture is heated to 130° C. for 2 hours.

Then, the mixture is cooled to 50° C., filtered and concentrated under vacuum at 140° C./1 mbar.

A solid with a melting point of 128°–134° C. is obtained after drying.

$\overline{Mn}$ (by GPC)=2712 g/mole $\overline{Mw}/\overline{Mn}$=1.41

Figure 1:
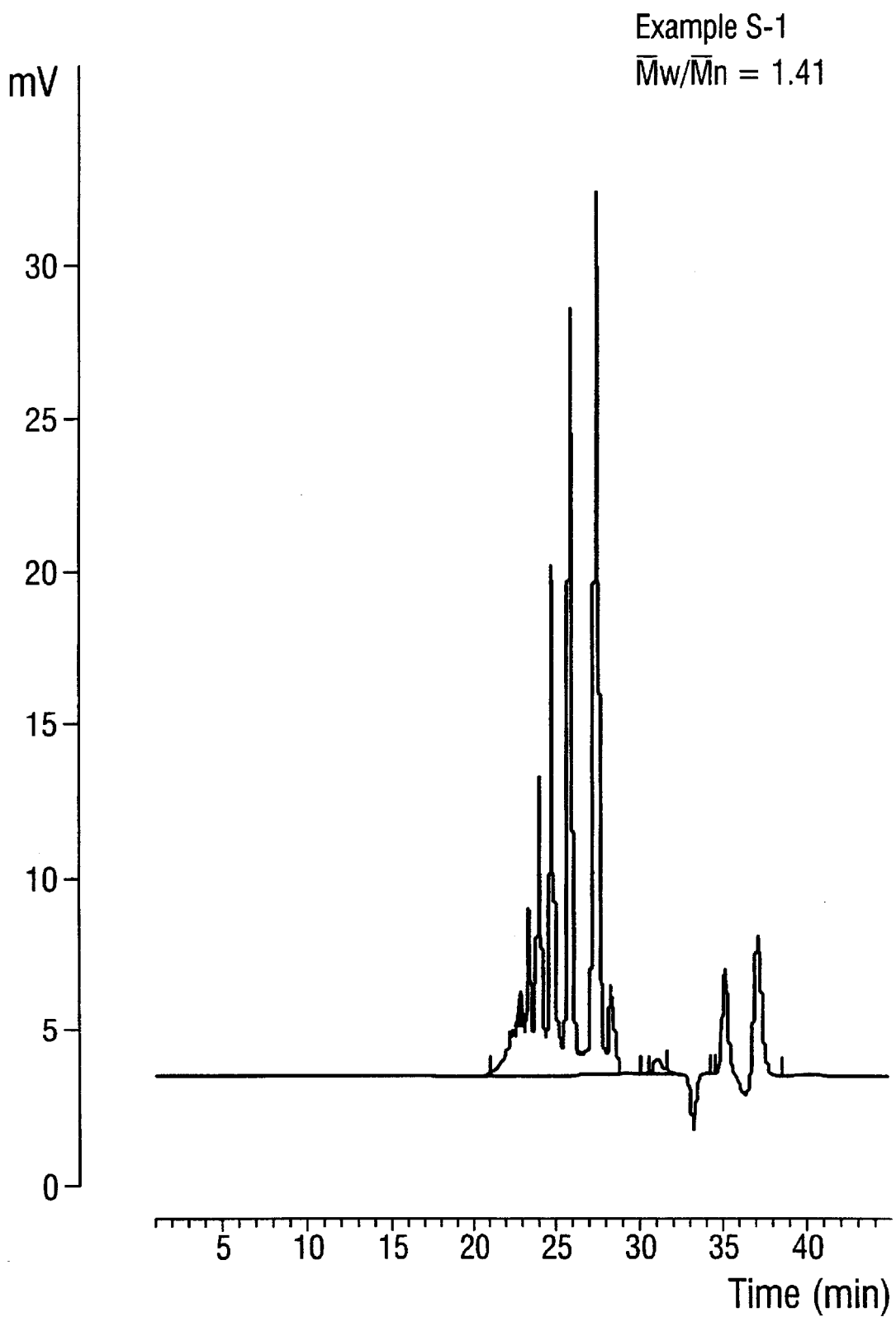
FIGS. 1 and 2 are Gel Permeation Chromatography chromatograms of the products obtained by Examples S-1 and S-2 respectively.

The GPC analysis shows a chromatogram as in FIG. 1.

The ratio of the three main single components ((n'=2): (n'=4):(n'=6)) of the polydispers product obtained is in molar % 2:0.93:0.4.

EXAMPLE S-2

Preparation of a product corresponding to the formula

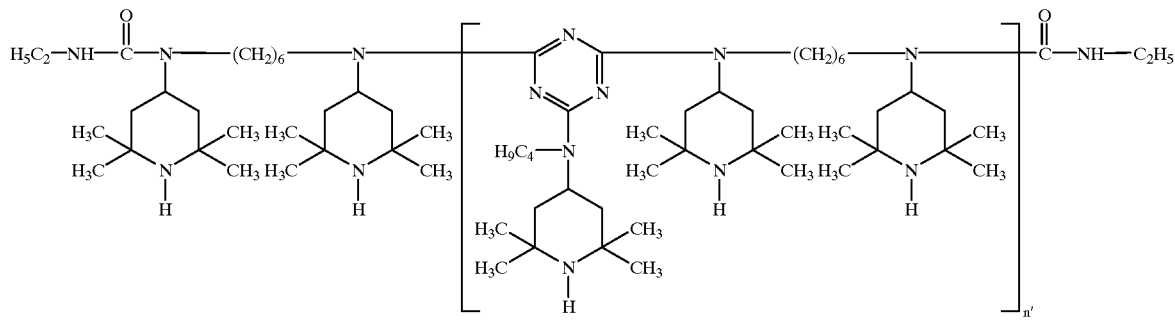

The product is prepared following the procedure described in Example S-1 using the appropriate reagents.

A solid with a melting point of 122°–130° C. is obtained.

$\overline{Mn}$ (by GPC)=2810 g/mole $\overline{Mw}/\overline{Mn}$=1.42

Figure 2:
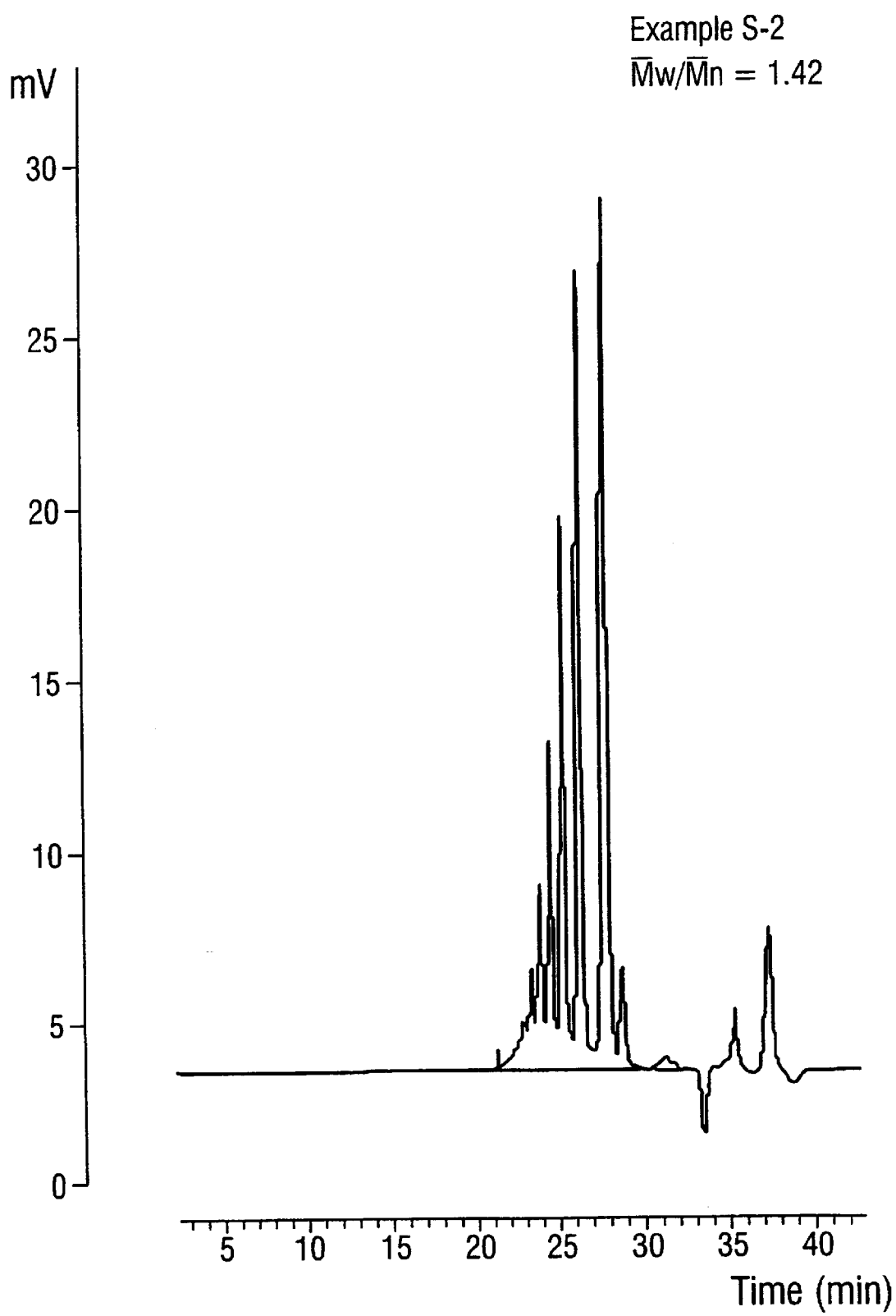

The GPC analysis shows a chromatogram as in FIG. 2.

The ratio of the three main single components ((n'=2): (n'=4):(n'=6)) of the polydispers product obtained is in molar % 2:0.84:0.32.

EXAMPLE 1

Preparation of a product corresponding to the formula

A magnetically stirred 200 ml 4-neck flask affixed with a ®Dean-Stark trap is charged with 7.0 g (0.0317 mole) of the product of Example S-1, 60 ml of cyclohexane and 0.1 9 of $MoO_3$. The content is heated to reflux. Then, 20.4 g (0.158 mole) of 70% t-butyl hydroperoxide is charged to an affixed addition funnel and added within 30 minutes. Reflux is continued for additional 30 minutes. The reaction mixture is transferred to a magnetically stirred ® Fisher-Porter pressure bottle along with additional 0.1 g of $MoO_3$. The content is heated at 120° C. for 3 hours at which point the red color of the nitroxyl intermediate dissipates to a pale yellow. $MoO_3$ is filtered and the filtrate is evaporated to a yellow glass. The yield is 10.1 g which is quantitative.

$^1$H-NMR: 0.84–2.5 ppm (broad, complex mixture); 3.2–3.44 ppm (s, broad, $NCH_2$); 3.54–3.70 ppm (s, broad, NOCH); 4.76–5.4 ppm (broad, NCH). Ratio of integration at 3.2, 3.54 and 4.76 ppm: 2:1:1.

$^{13}$C-NMR: 81.9 ppm (NOC); 165 ppm (triazine C)

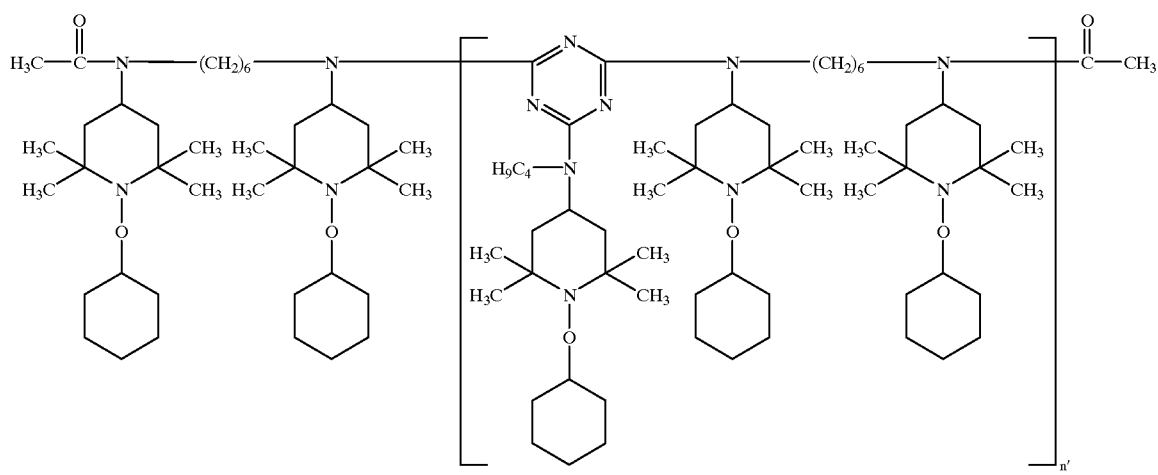

EXAMPLE 2
Preparation of a product corresponding to the formula

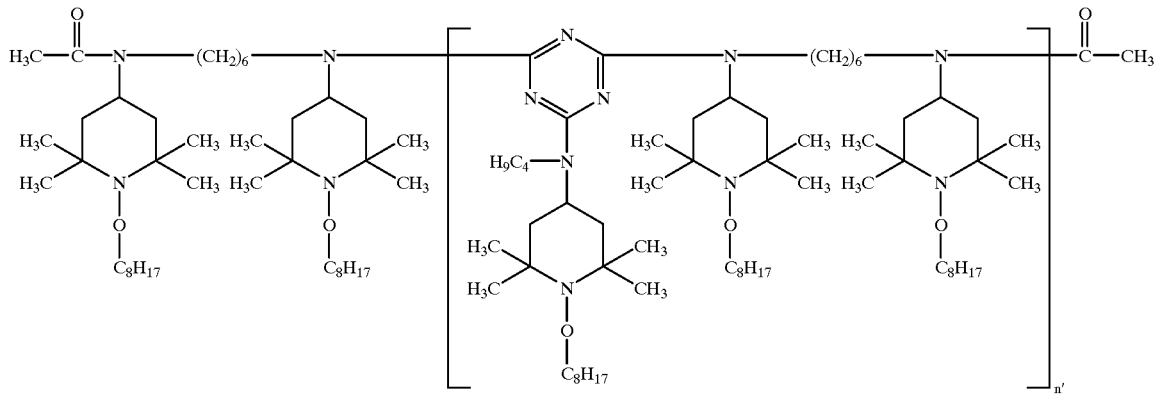

A 200 ml magnetically stirred 4-neck flask affixed with a ®Dean-Stark trap and an addition funnel is charged with 5.7 g (0.0258 mole) of the product of Example S-1, 50 ml of n-octane and 0.20 g of $MoO_3$. The content is heated to reflux. The addition funnel is charged with 16.6 g (0.129 mole) of 70% t-butyl hydroperoxide, which is added over a 30 minutes span. After additional 30 minutes of reflux, the reaction mixture is transferred to a magnetically stirred ®Fisher-Porter bottle. Then, additional 0.10 g of $MoO_3$ are added. The content is heated under pressure at 125° C. for three hours at which point the red color of the nitroxyl intermediate dissipates to a pale yellow. $MoO_3$ is filtered and the filtrate is evaporated to a pale yellow glass. The yield is 8.2 g (91% of theory).

$^1$H-NMR: 0.8–2.5 ppm (broad, complex mixture); 3.2–3.5 ppm (s, broad, $NCH_2$); 3.65–3.96 ppm (broad, NOCH); 4.9–5.4 ppm (s, broad, NCH). Ratio of integration at 3.2, 3.65 and 4.76 ppm is 2:1:1.

$^{13}$C-NMR: 78.7 ppm, 81.9 ppm and 83.2 ppm (NOC, mixture of isomers in $C_8H_{17}$); 165 ppm (triazine C).

EXAMPLE 3
Preparation of a product corresponding to the formula 7.0 g (0.0303 mole) of the product of Example S-2, 60 ml of cyclohexane and 0.20 g of $MoO_3$ are charged to a magnetically stirred 200 ml 4-neck flask affixed with a ®Dean-Stark trap, a condenser and an addition funnel. The content is heated to reflux. The addition funnel is charged with 19.5 g (0.152 mole) of 70% t-butyl hydroperoxide. The funnel content is added over a 30 minutes time span. The red color of the nitroxyl intermediate is observed. Reflux is continued for one hour. The reaction mixture is transferred to a magnetically stirred ®Fisher-Porter bottle along with additional 0.10 g of $MoO_3$. The content is heated under pressure at 125° C. for two hours, at which point the red color of the nitroxyl intermediate dissipates. $MoO_3$ is pressure filtered and the pale yellow filtrate is evaporated to a glass. The yield is 9.3 g (93% of theory).

$^1$H-NMR: 0.80–2.2 ppm (broad, complex mixture); 3.1–3.5 ppm (s, broad, $NCH_2$); 3.54–3.70 ppm (s, broad, NOCH); 4.90–5.4 ppm (broad, NCH). Ratio of integration at 3.2, 3.54 and 4.76 ppm: 2:1:1.

$^{13}$C-NMR: 81.8 ppm (NOC); 165 ppm (triazine C).

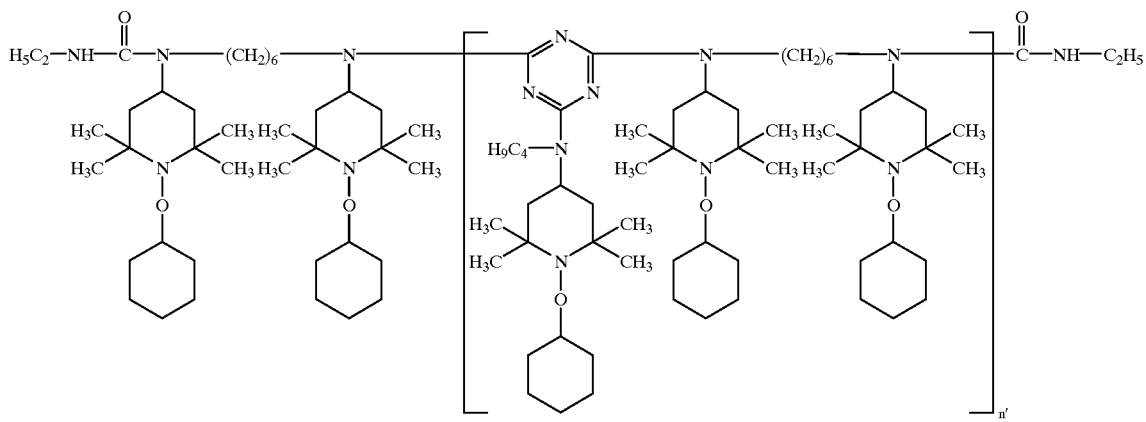

EXAMPLE 4
Preparation of a product corresponding to the formula

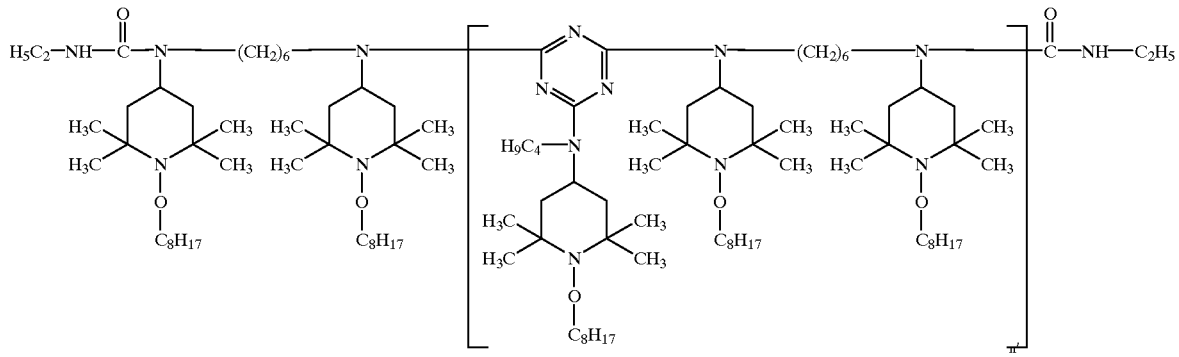

6.2 g (0.0268 mole) of the product of Example S-2, 50 ml of n-octane, and 0.10 g of $MoO_3$ are charged to a magnetically stirred 200 ml 4-neck flask affixed with a ®Dean-Stark trap, a condenser and an addition funnel. The content is heated to reflux. The addition funnel is charged with 17.3 g (0.134 mole) of 70% t-butyl hydroperoxide. The funnel content is added over a 30 minutes time span. The red color of the nitroxyl intermediate is observed. Reflux is continued for one hour. The reaction mixture is transferred to a magnetically stirred ®Fisher-Porter bottle along with additional 0.10 g of $MoO_3$. The content is heated under pressure at 125° C. for two hours, at which point the red color of the nitroxyl intermediate dissipates. $MoO_3$ is pressure filtered and the pale yellow filtrate is evaporated to a glass. The yield is 8.4 g (88% of theory).

$^1$H-NMR: 0.6–2.5 ppm (broad, complex mixture); 3.1–3.5 ppm (s, broad, $NCH_2$); 3.56–3.94 ppm (broad, NOCH); 4.9–5.4 ppm (s, broad, NCH). Ratio of integration at 3.1, 3.56 and 4.9 ppm is 2:1:1.

$^{13}$C-NMR: 78.5 ppm, 81.8 ppm and 83.2 ppm (NOC, mixture of isomers in $C_8H_{17}$); 165 ppm (triazine C).

EXAMPLE A

Pigmented thermoplastic olefin (TPO) pellets are prepared by mixing a polyolefin blend (polypropylene containing an ethylene-propylene copolymer; ®Polytrope TPP 518-01 from ®A. Schulman, Inc.; Akron, Ohio, USA) with the additives listed below in a ®Superior/MPM 1" single screw extruder with a general all-purpose screw (24:1 L/D) at 200° C., cooling in a water bath and pelletizing. Prior to extrusion and molding, the additives are dry blended in a tumble dryer.

Additives:
- 0.25%*) of ®Red 3B (Pigment Red 177, Color Index 65300),
- 0.05%*) of pentaerythritol tetrakis[3-(3,5-di-tert-butyl-4-hydroxyphenyl) propionate],
- 0.05%*) of this[2,4-di -tert-butylphenyl] phosphate,
- 0.2%*) of 2-(2'-hydroxy-3',5'-di-tert-amylphenyl) benztriazol,
- 0.2%*) of bis(a-octyloxy-2,2,6,6-tetramethyl-4-piperidyl) sebacate,
- 0.1%*) of calcium stearate, about 10%*) of talc and
- 0.2%*) of the product of Example 1, 2, 3 or 4

*) weight percent based on the polyolefin blend

The resulting pellets are molded into 1.524 mm thick 2"×2" plaques at about 190° C. on a ®BOY 30M Injection Molding Machine.

The test plaques are mounted in metal frames and exposed in an ®Atlas Ci65 Xenon Arc Weather-O-meter at 70° C. black panel temperature, 0.55 $W/m^2$ at 340 nanometers and 50% relative humidity with intermittent light/dark cycles and water spray (®Society of Automotive Engineers—SAE J 1960 Test Procedure—Exterior Automotive conditions).

The specimens are tested at approximately 625 kilojoule intervals by performing color measurements on an Applied Color Systems spectrophotometer by reflectance mode according to ASTM D 2244-79. Gloss measurements are conducted on ®BYK-GARDNER Haze/Gloss Meter at 60° according to ASTM D 523.

The stabilized samples show good gloss retention and good resistance to color change upon UV exposure.

What is claimed is:

1. A compound of the formula (I)

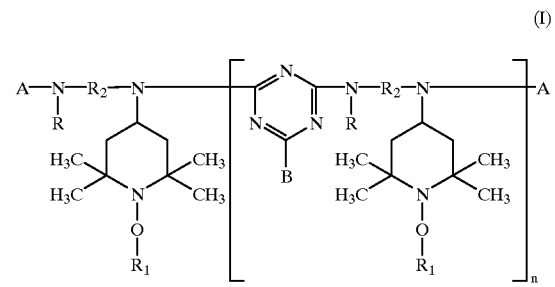

wherein n is a number from 2 to 14;

the radicals $R_1$ are independently of one another hydrogen or a hydrocarbyl radical or —O—R, is oxyl;

the radicals $R_2$ are independently of one another $C_2$-$C_{12}$alkylene, $C_4$-$C_{12}$alkenylene, $C_5$-$C_7$cycloalkylene, $C_5$-$C_7$cycloalkylenedi($C_1$-$C_4$alkylene), $C_1$-$C_4$alkylenedi($C_5$-$C_7$cycloalkylene), phenylenedi($C_1$-$C_4$alkylene) or $C_4$-$C_{12}$alkylene interrupted by 1,4-piperazinediyl, —O— or >N—$X_1$ with $X_1$ being $C_1$-$C_{12}$acyl or ($C_1$-$C_{12}$alkoxy)carbonyl or having one of the definitions of $R_4$ given below except hydrogen; or $R_2$ is a group of the formula (a), (b) or (c);

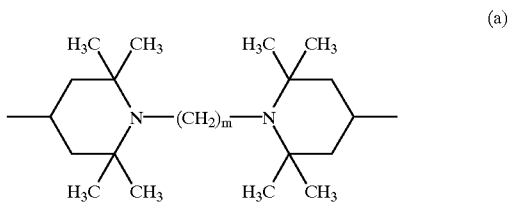

(a)

(b)

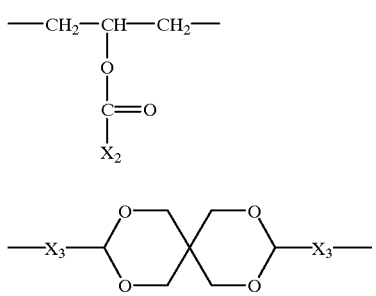

(c)

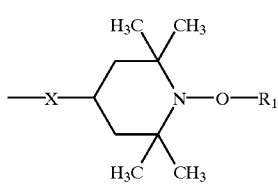

with m being 2 or 3,

X$_2$ being C$_1$–C$_{18}$alkyl, C$_5$–C$_{12}$cycloalkyl which is unsubstituted or substituted by 1, 2 or 3 C$_1$–C$_4$alkyl; phenyl which is unsubstituted or substituted by 1, 2 or 3 C$_1$–C$_4$alkyl or C$_1$–C$_4$alkoxy; C$_7$–C$_9$phenylalkyl which is unsubstituted or substituted on the phenyl by 1, 2 or 3 C$_1$–C$_4$alkyl; and the radicals X$_3$ being independently of one another C$_2$–C$_{12}$alkylene;

the radicals A are independently of one another C$_1$–C$_8$acyl, (C$_1$–C$_8$alkoxy)carbonyl, (C$_5$–C$_{12}$cycloalkoxy)carbonyl, (C$_1$–C$_8$alkyl)aminocarbonyl, (C$_5$–C$_{12}$cycloalkyl)aminocarbonyl, (C$_7$–C$_9$phenylalkyl)aminocarbonyl, C$_1$–C$_8$alkyl, C$_5$–C$_{12}$cycloalkyl which is unsubstituted or substituted by 1, 2 or 3 C$_1$–C$_4$alkyl; C$_3$–C$_6$alkenyl, C$_7$–C$_9$phenylalkyl which is unsubstituted or substituted on the phenyl by 1, 2 or 3 C$_1$–C$_4$alkyl; or —CH$_2$CN;

B is —OR$_3$, —N(R$_4$)(R$_5$) or a group of the formula (II);

(II)

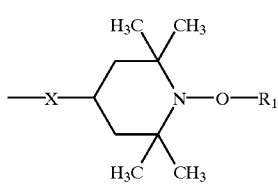

R$_3$, R$_4$ and R$_5$, which are identical or different, are hydrogen, C$_1$–C$_{18}$alkyl, C$_5$–C$_{12}$cycloalkyl which is unsubstituted or substituted by 1, 2 or 3 C$_1$–C$_4$alkyl; C$_3$–C$_{18}$alkenyl, phenyl which is unsubstituted or substituted by 1, 2 or 3 C$_1$–C$_4$alkyl or C$_1$–C$_4$alkoxy; C$_7$–C$_9$phenylalkyl which is unsubstituted or substituted on the phenyl by 1, 2 or 3 C$_1$–C$_4$alkyl; tetrahydrofurfuryl or C$_2$–C$_4$alkyl which is substituted in the 2, 3 or 4 position by —OH, C$_1$–C$_8$alkoxy, di(C$_1$–C$_4$alkyl)amino or a group of the formula (III);

(III)

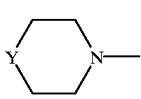

with Y being —O—, —CH$_2$—, —CH$_2$CH$_2$— or >N—CH$_3$, or —N(R$_4$)(R$_5$) is additionally a group of the formula (III);

X is —O— or >N—R$_6$;

R$_6$ is hydrogen, C$_1$–C$_{18}$alkyl, C$_3$–C$_{18}$alkenyl, C$_5$–C$_{12}$cycloalkyl which is unsubstituted or substituted by 1, 2 or 3 C$_1$–C$_4$alkyl; C$_7$–C$_9$phenylalkyl which is unsubstituted or substituted on the phenyl by 1, 2 or 3 C$_1$–C$_4$alkyl; tetrahydrofurfuryl, a group of the formula (IV), (IV)

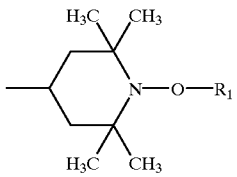

or C$_2$–C$_4$alkyl which is substituted in the 2, 3 or 4 position by —OH, C$_1$–C$_8$alkoxy, di(C$_1$–C$_4$alkyl)amino or a group of the formula (III); and the radicals R have independently of one another one of the meanings given for R$_6$;

with the proviso that in the individual recurrent units of the formula (I), each of the radicals B, R, R$_1$ and R$_2$ has the same or a different meaning.

2. A compound of the formula (i) according to claim 1, wherein R is a group of the formula (IV).

3. A compound of the formula (I) according to claim 1, wherein R$_1$ is hydrogen, C$_1$–C$_{18}$alkyl, C$_5$–C$_{18}$alkenyl, C$_5$–C$_{18}$alkynyl, C$_5$–C$_{12}$cycloalkyl unsubstituted or substituted by C$_1$–C$_4$alkyl; C$_5$–C$_{12}$cycloalkenyl unsubstituted or substituted by C$_1$–C$_4$alkyl; a bicyclic or tricyclic hydrocarbyl having 6 to 10 carbon atoms or C$_7$–C$_9$phenylalkyl unsubstituted or substituted on the phenyl by C$_1$–C$_4$alkyl; or —O—R$_1$ is oxyl.

4. A compound of the formula (I) according to claim 1, wherein R$_1$ is hydrogen, C$_1$–C$_8$alkyl, C$_5$–C$_8$cycloalkyl unsubstituted or substituted by methyl; cyclohexenyl, α-methylbenzyl or 1,2,3,4-tetrahydronaphthenyl.

5. A compound of the formula (I) according to claim 1, wherein R$_1$ is methyl, octyl or cyclohexyl.

6. A compound of the formula (I) according to claim 1, wherein A is acetyl, (C$_1$–C$_4$alkoxy)carbonyl, (C$_1$–C$_4$alkyl)aminocarbonyl or C$_1$–C$_4$alkyl.

7. A compound of the formula (I) according to claim 1, wherein R$_2$ is C$_2$–C$_{12}$alkylene, C$_5$–C$_7$cycloalkylene, C$_5$–C$_7$cycloalkylenedi(C$_1$–C$_4$alkylene), C$_1$–C$_4$alkylenedi(C$_5$–C$_7$cycloalkylene) or phenylenedi(C$_1$–C$_4$alkylene); A is C$_1$–C$_8$acyl, (C$_1$–C$_8$alkoxy)carbonyl, (C$_5$–C$_7$cycloalkoxy)carbonyl, (C$_1$–C$_4$alkyl)aminocarbonyl, (C$_5$–C$_7$cycloalkyl)aminocarbonyl, benzylaminocarbonyl, C$_1$–C$_6$alkyl, C$_5$–C$_7$cycloalkyl, allyl or benzyl;

R$_3$, R$_4$ and R$_5$, which are identical or different, are hydrogen, C$_1$–C$_{12}$alkyl, C$_5$–C$_7$cycloalkyl which is unsubstituted or substituted by 1, 2 or 3 C$_1$–C$_4$alkyl; C$_3$–C$_{12}$alkenyl, phenyl which is unsubstituted or substituted by 1, 2 or 3 C$_1$–C$_4$alkyl; benzyl which is unsubstituted or substituted on the phenyl by C$_1$–C$_4$alkyl; tetrahydrofurfuryl or C$_2$–C$_3$alkyl which is substituted in the 2 or 3 position by —OH, C$_1$–C$_4$alkoxy, di(C$_1$–C$_4$alkyl)amino or a group of the formula (III); or —N(R$_4$)(R$_5$) is additionally a group of the formula (III); and R$_6$ is hydrogen, C$_1$–C$_{12}$alkyl, C$_5$–C$_7$cycloalkyl which is unsubstituted or substituted by 1, 2 or 3 C$_1$–C$_4$alkyl; benzyl which is unsubstituted or substituted on the phenyl by 1, 2 or 3 C$_1$–C$_4$alkyl; tetrahydrofurfuryl, a group of the formula (IV) or C$_2$–C$_3$alkyl which is substituted in the 2 or 3 position by —OH, $C_1$–$C_4$alkoxy, di($C_1$–$C_4$alkyl)amino or a group of the formula (III).

8. A compound of the formula (I) according to claim 1, wherein $R_2$ is $C_2$–$C_8$alkylene;

A is $C_1$–$C_8$acyl, ($C_1$–$C_4$alkoxy)carbonyl, cyclohexoxycarbonyl, ($C_1$–$C_4$alkyl)aminocarbonyl, cyclohexylaminocarbonyl, benzylaminocarbonyl, $C_1$–$C_4$alkyl, cyclohexyl, allyl or benzyl;

$R_3$, $R_4$ and $R_5$, which are identical or different, are hydrogen, $C_1$–$C_8$alkyl, cyclohexyl which is unsubstituted or substituted by methyl; $C_3$–$C_8$alkenyl, phenyl which is unsubstituted or substituted by methyl; benzyl, tetrahydrofurfuryl or $C_2$–$C_3$alkyl substituted in the 2 or 3 position by —OH, $C_1$–$C_4$alkoxy, dimethylamino, diethylamino or 4-morpholinyl; or —N($R_4$)($R_5$) is additionally 4-morpholinyl; and $R_6$ is hydrogen, $C_1$–$C_8$alkyl, cyclohexyl which is unsubstituted or substituted by methyl;

benzyl, tetrahydrofurfuryl, a group of the formula (IV) or $C_2$–$C_3$alkyl substituted in the 2 or 3 position by —OH, $C_1$–$C_4$alkoxy, dimethylamino, diethylamino or 4-morpholinyl.

9. A compound of the formula (I) according to claim 1, wherein n is a number from 2 to 6;

R is a group of the formula (IV);

$R_2$ is $C_2$–$C_6$alkylene;

A is $C_{1–C8}$acyl, ($C_1$–$C_8$alkoxy)carbonyl, ($C_1$–$C_4$alkyl) aminocarbonyl, $C_1$–$C_4$alkyl or allyl;

B is —N($R_4$)($R_5$) or a group of the formula (II);

$R_4$ and $R_5$, which are identical or different, are hydrogen, $C_1$–$C_8$alkyl, 2-hydroxyethyl or 2-methoxyethyl or —N($R_4$)($R_5$) is additionally 4-morpholinyl;

X is >$NR_6$; and $R_6$ is $C_1$–$C_4$alkyl.

10. A compound of the formula (I) according to claim 1, wherein n is a number from 2 to 6;

R is a group of the formula (IV);

$R_1$ is methyl, octyl or cyclohexyl;

$R_2$ is $C_2$–$C_6$alkylene;

A is $C_1$–$C_8$acyl, ($C_1$–$C_8$alkoxy)carbonyl, ($C_1$–$C_4$alkyl) aminocarbonyl or $C_1$–$C_4$alkyl;

B is —N($R_4$)($R_5$) or a group of the formula (II);

$R_4$ and $R_5$, which are identical or different, are $C_1$–$C_8$alkyl or —N($R_4$)($R_5$) is additionally 4-morpholinyl;

X is >$NR_6$; and $R_6$ is $C_1$–$C_4$alkyl.

11. A compound of the formula (I) according to claim 1, wherein n is a number from 2 to 6;

R is a group of the formula (IV);

$R_1$ is methyl, octyl or cyclohexyl;

$R_2$ is $C_2$–$C_6$alkylene;

A is $C_1$–$C_8$acyl or ($C_1$–$C_4$alkyl)aminocarbonyl;

B is a group of the formula (II);

X is >$NR_6$; and $R_6$ is $C_1$–$C_4$alkyl.

12. A product obtainable by transferring groups of the formula (IV-0)

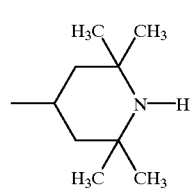

(IV-0)

being present in a block oligomer corresponding to the formula (I-0)

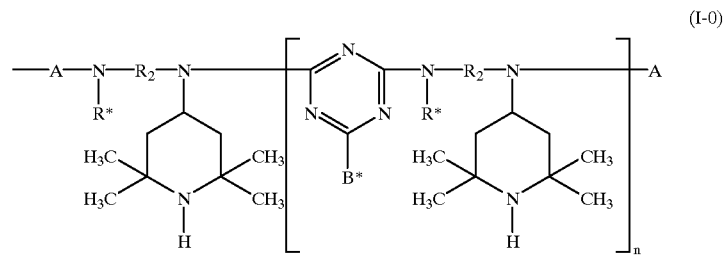

(I-0)

to groups of the formula (IV);

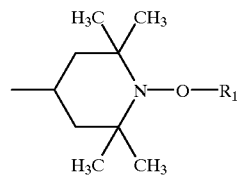

(IV)

wherein $R_1$ is a hydrocarbyl radical or —O—$R_1$ is oxyl;

said transfer is carried out by reaction of the block oligomer corresponding to the formula (I-0) with a hydroperoxide in a hydrocarbon solvent in the presence of a peroxide decomposing catalyst;

n is a number from 2 to 14;

the radicals $R_2$ are independently of one another $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi-($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_4$ given below; or $R_2$ is a group of the formula (a), (b) or (c);

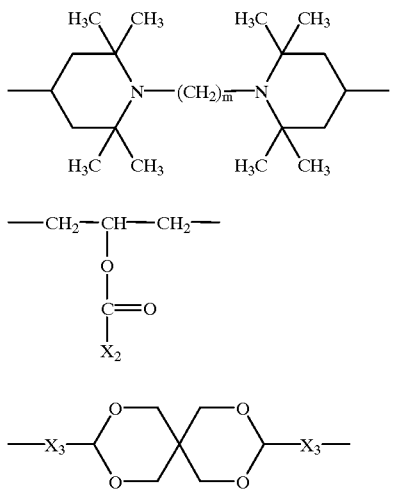

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

the radicals A are independently of one another $C_1$–$C_8$acyl, ($C_1$–$C_8$alkoxy)carbonyl, ($C_5$–$C_{12}$cycloalkoxy)carbonyl, ($C_1C_8$alkyl)aminocarbonyl, ($C_5$–$C_{12}$cycloalkyl)aminocarbonyl, ($C_7$–$C_9$phenylalkyl)aminocarbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; or —$CH_2CN$;

B* is —$OR_3$, —$N(R_4)(R_5)$ or a group of the formula (II-0);

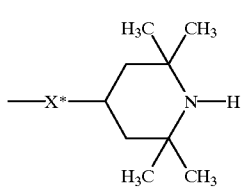

$R_3$, $R_4$ and $R_5$, which are identical or different, are $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

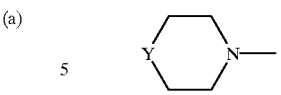

with Y being —O—, —$OH_2$—, —$CH_2CH_2$— or >N—$CH_3$;

and $R_3$ is additionally hydrogen or —$N(R_4)(R_5)$ is additionally a group of the formula (III);

X* is —O— or >N—$R_6$*;

$R_6$* is $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV-0), or $C_2$–$C_4$alkyl which is substituted in the 2, 3 or 4 position by —OH, $C_1$–$C_8$alkoxy, di($C_1$–$C_4$alkyl)amino or a group of the formula (III); and the radicals R* have independently of one another one of the meanings given for $R_6$*;

with the proviso that in the individual recurrent units of the formula (I-0), each of the radicals B*, R* and $R_2$ has the same or a different meaning.

13. A product according to claim 12, wherein
$R_2$ is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by —O— or >N—$X_1$ with $X_1$ being $C_1$–$C_{12}$acyl or ($C_1$–$C_{12}$alkoxy)carbonyl or having one of the definitions of $R_4$; or $R_2$ is a group of the formula (b);

$R_3$, $R_4$ and $R_5$, which are identical or different, are $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and $R_3$ is additionally hydrogen or —$N(R_4)(R_5)$ is additionally a group of the formula (III);

$R_6$* is $C_1$–$C_{18}$alkyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; or a group of the formula (IV-0).

14. A product according to claim 12, wherein the block oligomer corresponding to the formula (I-0) has a polydispersity $\overline{Mw}/\overline{Mn}$ of 1 to 1.7.

15. A product according to claim 12, wherein $R_1$ is $C_5$–$C_{18}$alkyl, $C_5$–$C_{18}$alkenyl, $C_5$–$C_{18}$alkynyl, $C_5$–$C_{12}$cycloalkyl unsubstituted or substituted by $C_1$–$C_4$alkyl; $C_5$–$C_{12}$cycloalkenyl unsubstituted or substituted by $C_1$–$C_4$alkyl; a bicyclic or tricyclic hydrocarbyl having 6 to 10 carbon atoms or $C_7$–$C_9$phenylalkyl unsubstituted or substituted on the phenyl by $C_1$–$C_4$alkyl; and the hydrocarbon solvent is, dependent on $R_1$, $C_5$–$C_{18}$alkane, $C_5$–$C_{18}$alkene, $C_5$–$C_{18}$alkyne, $C_5$–$C_{12}$cycloalkane unsubstituted or substituted by $C_1$–$C_4$alkyl; $C_5$–$C_{12}$cycloalkene unsubstituted or substituted by $C_1$–$C_4$alkyl; a bicyclic or tricyclic hydrocarbon having 6 to 10 carbon atoms or $C_7$–$C_9$phenylalkane unsubstituted or substituted on the phenyl by $C_1$–$C_4$alkyl.

16. A product according to claim 12, wherein the radical —O—R$_1$ is oxyl and the hydrocarbon solvent is an inert organic solvent.

17. A product according to claim 12, wherein the peroxide decomposing catalyst is a metal carbonyl, metal oxide, metal acetylacetonate or a metal alkoxide where the metal is selected from the groups IVb, Vb, VIb, VIIb and VIII of the periodic table.

18. A product according to claim 12, wherein the hydroperoxide is t-butyl hydroperoxide and the peroxide decomposing catalyst is MoO$_3$.

19. A product according to claim 12, wherein per mole of the group of the formula (IV-0)

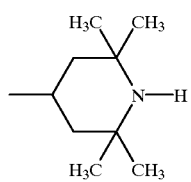

(IV-0)

being present in the block oligomer of the formula (I-0) 2 to 8 moles of the hydroperoxide, 0.001 to 0.1 mole of the peroxide decomposing catalyst and 5 to 30 moles of the hydrocarbon solvent are applied.

20. A product obtainable by hydrogenating a product according to claim 12, wherein —OR$_1$ in the formula (IV) is oxyl to obtain a block oligomer with groups of the formula (IV-1).

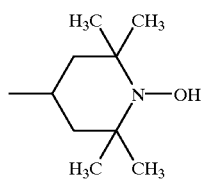

(IV-1)

21. A mixture containing a) a compound of the formula (Ia),

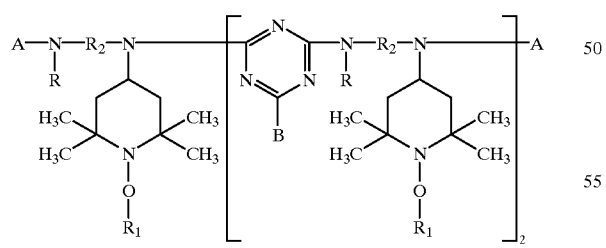

(Ia)

b) a compound of the formula (Ib) and

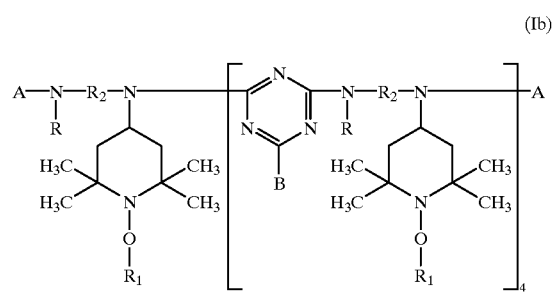

(Ib)

c) a compound of the formula (Ic)

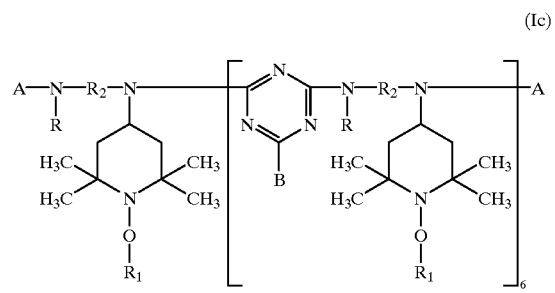

(Ic)

wherein the compounds of the formulae (Ia), (Ib) and (Ic) differ only in the number of the repetitive units, the molar ratio of the compounds of the formula (Ia) to (Ib) to (Ic) is 2:2:1.5 to 2:0.5:0.05; and R$_1$ is hydrogen or a hydrocarbyl radical or —O—R$_1$ is oxyl;

R$_2$ is C$_2$-C$_{12}$alkylene, C$_4$-C$_{12}$alkenylene, C$_5$-C$_7$cycloalkylene, C$_5$-C$_7$cycloalkylenedi(C$_1$-C$_4$alkylene), C$_1$-C$_4$alkylenedi(C$_5$-C$_7$cycloalkylene), phenylenedi(C$_1$-C$_4$alkylene) or C$_4$-C$_{12}$alkylene interrupted by 1,4-piperazinediyl, —O— or >N—X$_1$ with X$_1$ being C$_1$-C$_{12}$acyl or (C$_1$-C$_{12}$alkoxy)carbonyl or having one of the definitions of R$_4$ given below; or R$_2$ is a group of the formula (a), (b) or (c);

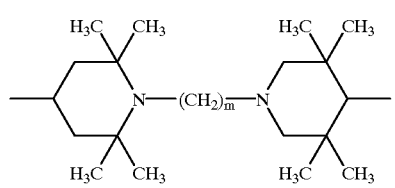

(a)

-continued (b)

—CH$_2$—CH—CH$_2$—
　　　　|
　　　　O
　　　　|
　　　　C=O
　　　　|
　　　　X$_2$

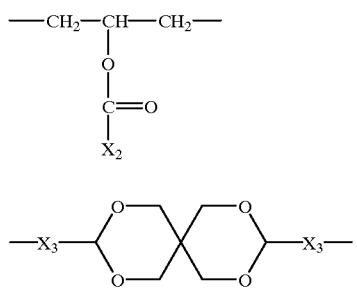
(c)

with m being 2 or 3,

X$_2$ being C$_1$–C$_{18}$alkyl, C$_5$–C$_{12}$cycloalkyl which is unsubstituted or substituted by 1, 2 or 3 C$_1$–C$_4$alkyl; phenyl which is unsubstituted or substituted by 1, 2 or 3 C$_1$–C$_4$alkyl or C$_1$–C$_4$alkoxy; C$_7$–C$_9$phenylalkyl which is unsubstituted or substituted on the phenyl by 1, 2 or 3 C$_1$–C$_4$alkyl; and the radicals X$_3$ being independently of one another C$_2$–C$_{12}$alkylene;

A is C$_1$–C$_8$acyl, (C$_1$–C$_8$alkoxy)carbonyl, (C$_5$–C$_{12}$cycloalkoxy)carbonyl, (C$_1$–C$_8$alkyl)aminocarbonyl, (C$_5$–C$_{12}$cycloalkyl)aminocarbonyl, (C$_7$–C$_9$phenylalkyl)aminocarbonyl, C$_1$–C$_8$alkyl, C$_5$–C$_{12}$cycloalkyl which is unsubstituted or substituted by 1, 2 or 3 C$_1$–C$_4$alkyl; C$_3$–C$_6$alkenyl, C$_7$–C$_9$phenylalkyl which is unsubstituted or substituted on the phenyl by 1, 2 or 3 C$_1$–C$_4$alkyl; or —CH$_2$CN;

B is —OR$_3$, —N(R$_4$)(R$_5$) or a group of the formula (II);

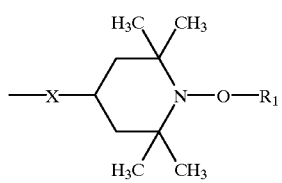
(II)

R$_3$, R$_4$ and R$_5$, which are identical or different, are C$_1$–C$_{18}$alkyl, C$_5$–C$_{12}$cycloalkyl which is unsubstituted or substituted by 1, 2 or 3 C$_1$–C$_4$alkyl; C$_3$–C$_{18}$alkenyl, phenyl which is unsubstituted or substituted by 1, 2 or 3 C$_1$–C$_4$alkyl or C$_1$–C$_4$alkoxy; C$_7$–C$_9$phenylalkyl which is unsubstituted or substituted on the phenyl by 1, 2 or 3 C$_1$–C$_4$alkyl; tetrahydrofurfuryl or C$_2$–C$_4$alkyl which is substituted in the 2, 3 or 4 position by —OH, C$_1$–C$_8$alkoxy, di(C$_1$–C$_4$alkyl)amino or a group of the formula (III);

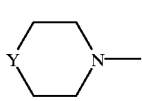
(III)

with Y being —O—, —CH$_2$—, —CH$_2$CH$_2$— or >N—CH$_3$; and R$_3$ is additionally hydrogen or —N(R$_4$)(R$_5$) is additionally a group of the formula (III);

X is —O— or >N—R$_6$;

R$_6$ is C$_1$–C$_{18}$alkyl, C$_3$–C$_{18}$alkenyl, C$_5$–C$_{12}$cycloalkyl which is unsubstituted or substituted by 1, 2 or 3 C$_1$–C$_4$alkyl; C$_7$–C$_9$phenylalkyl which is unsubstituted or substituted on the phenyl by 1, 2 or 3 C$_1$–C$_4$alkyl; tetrahydrofurfuryl, a group of the formula (IV),

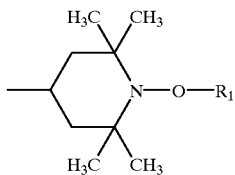
(IV)

or C$_2$–C$_4$alkyl which is substituted in the 2, 3 or 4 position by —OH, C$_1$–C$_8$alkoxy, di(C$_1$–C$_4$alkyl)amino or a group of the formula (III); and R has one of the meanings given for R$_6$.

22. A mixture according to claim 21, wherein

R is a group of the formula (IV);

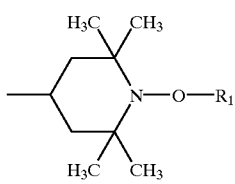
(IV)

R$_1$ is octyl or cyclohexyl;

R$_2$ is C$_2$–C$_6$alkylene;

A is C$_1$–C$_8$acyl or (C$_1$–C$_4$alkyl)aminocarbonyl;

B is a group of the formula (II);

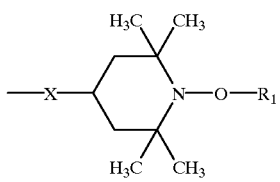
(II)

X is >NR$_6$; and

R$_6$ is C$_1$–C$_4$alkyl.

23. A composition containing an organic material susceptible to degradation induced by light, heat or oxidation and a compound according to claim 1.

24. A composition according to claim 23, wherein the organic material is a synthetic polymer.

25. A composition according to claim 23, wherein the organic material is polyethylene or polypropylene.

26. A composition containing an organic material susceptible to degradation induced by light, heat or oxidation and a product according to claim 12.

27. A method for stabilizing an organic material against degradation induced by light, heat or oxidation, which comprises incorporating into said organic material a product according to claim 1.

* * * * *